(12) United States Patent
Tonomura et al.

(10) Patent No.: US 9,567,354 B2
(45) Date of Patent: Feb. 14, 2017

(54) AMINO ACID-MODIFIED SILANE COMPOUNDS AND MAKING METHOD

(75) Inventors: Yoichi Tonomura, Joetsu (JP); Tohru Kubota, Joetsu (JP); Takayuki Honma, Joetsu (JP)

(73) Assignee: SHIN-ETSU CHEMICAL CO., LTD., Tokyo (JP)

(*) Notice: Subject to any disclaimer, the term of this patent is extended or adjusted under 35 U.S.C. 154(b) by 579 days.

(21) Appl. No.: 13/370,426

(22) Filed: Feb. 10, 2012

(65) Prior Publication Data

US 2012/0209020 A1     Aug. 16, 2012

(30) Foreign Application Priority Data

Feb. 10, 2011 (JP) ................................. 2011-026789
Sep. 7, 2011 (JP) ................................. 2011-194619

(51) Int. Cl.
*C07F 7/18* (2006.01)

(52) U.S. Cl.
CPC ............. *C07F 7/184* (2013.01); *C07F 7/1816* (2013.01); *C07F 7/1836* (2013.01); *C07F 7/1844* (2013.01)

(58) Field of Classification Search
CPC ................................ C07F 7/184; C07F 7/1816
USPC .................................................. 556/425, 413
See application file for complete search history.

(56) References Cited

U.S. PATENT DOCUMENTS

| 5,936,703 A | 8/1999 | Miyazaki et al. |
| 2010/0166665 A1 | 7/2010 | Butts et al. |
| 2010/0297049 A1 | 11/2010 | Samain et al. |

FOREIGN PATENT DOCUMENTS

| CN | 101812086 A | 8/2010 |
| JP | 59-201064 A | 11/1984 |
| JP | 63-500991 A | 4/1988 |
| JP | 5-222064 A | 8/1993 |
| JP | 08-325555 A | 12/1996 |
| JP | 8-325555 A | 12/1996 |
| JP | 2011-246391 A | 12/2011 |
| WO | 87/06470 A1 | 11/1987 |
| WO | 95/10523 A1 | 4/1995 |
| WO | 2010/076237 A2 | 7/2010 |

OTHER PUBLICATIONS

Office Action dated Mar. 26, 2015, issued in corresponding Chinese Patent Application No. 201210105295.X, w/ English translation. (17 pages).
Bianco, Alberto et al., "Hydrolysis Rate of Functionalized Fullerenes Bearing Alkoxysilanes: A Comparative Study". Eur. J. Org. chem. May 2006, pp. 2934-2941.
Japanes Office Action dated Sep. 24, 2014, issued in corresponding JP application No. 2011-194619 (3 pages).
Alberto Bianco et al., "Hydrolysis Rate of Functionalized Fullerenes Bearing Alkoxysilanes: A Comparative Study" Eur. J. Chem. 2006, pp. 2934-2941, Wiley-VCH Verlag GmbH & Co. KGaA, Weinheim, issued in Japanes Office Action dated Sep. 24, 2014 (8 pages).
Office Action dated Mar. 31, 2015, issued in corresponding Japanese Application No. 2011-194619, (3 pages).
Practical Plastics Glossary, Plactics Age Co;, Ltd., Silane coupling agent, 1989, p. 304.

*Primary Examiner* — Shawquia Jackson
(74) *Attorney, Agent, or Firm* — Westerman, Hattori, Daniels & Adrian, LLP

(57) ABSTRACT

Novel amino acid-modified silane compounds having a weakly acidic amino group and a weakly basic carboxyl group are useful as a surface treating agent or textile treating agent.

3 Claims, 10 Drawing Sheets

AMINO ACID-MODIFIED SILANE COMPOUNDS AND MAKING METHOD

CROSS-REFERENCE TO RELATED APPLICATION

This non-provisional application claims priority under 35 U.S.C. §119(a) on Patent Application Nos. 2011-026789 and 2011-194619 filed in Japan on Feb. 10, 2011 and Sep. 7, 2011, respectively, the entire contents of which are hereby incorporated by reference.

TECHNICAL FIELD

This invention relates to novel amino acid-modified silane compounds and a method for preparing the same. These silane compounds are useful as paint additives, adhesives, silane coupling agents, textile treating agents, surface treating agents, and the like.

BACKGROUND ART

Amino-containing silane compounds are known useful as surface treating agents which are applied to substrates to render their surfaces hydrophilic and as textile treating agents which are applied to fibers and fabrics to impart hydrophilic properties. Exemplary compounds include aminopropyltrimethoxysilane, aminopropylmethyldimethoxysilane, aminoethylaminopropyltrimethoxysilane, and aminoethylaminopropylmethyldimethoxysilane. While these amino-containing silane compounds can impart hydrophilic properties, they are less effective for imparting antifouling and antifungal properties to the treated surface.

Also known are those compounds capable of imparting not only hydrophilic, but also antifouling and antifungal properties to the treated surface. For example, Patent Document 1 discloses silane compounds having a tetraalkylammonium group such as 3-(trimethoxysilyl)propyloctadecyldimethylammonium chloride. Patent Documents 1 and 2 disclose silane compounds containing a sulfobetaine group and silane compounds containing quaternary ammonium and carboxyl groups.

However, these compounds are still unsatisfactory. Although the tetraalkylammonium-containing silane compounds described in Patent Document 1 can impart antifungal properties, they fail to impart satisfactory antifouling properties because the treated surfaces of substrates or fabrics are electrostatically charged positive by the tetraalkylammonium group, allowing dust and debris to deposit on the surface owing to electrostatic adsorption. Since the sulfobetaine-containing silane compounds described in Patent Documents 2 and 3 and the silane compounds containing tetraalkylammonium and carboxyl groups described in Patent Document 3 form a zwitter-ion in the molecule, the treated surfaces of substrates or fabrics are less electrostatically charged than the treatment with the tetraalkylammonium-containing silane compounds. The sulfobetaine-containing silane compounds have a bias toward the negative charge side due to the sulfonic acid group which is a strong acid, and the silane compounds containing tetraalkylammonium and carboxyl groups have a bias toward the positive charge side due to the tetraalkylammonium group. Because of such a bias from electrical neutrality, no satisfactory antifouling properties are available.

CITATION LIST

Patent Document 1: JP-A S63-500991 (WO 87/06470)
Patent Document 2: JP-A H05-222064
Patent Document 3: WO 1995/10523 (U.S. Pat. No. 5,936,703)

DISCLOSURE OF INVENTION

An object of the invention is to provide amino acid-modified silane compounds capable of imparting satisfactory antifouling and hydrophilic properties and a method for preparing the same.

The inventors have found that a certain amino acid-modified silane compound exhibits improved hydrophilic and antifouling properties since it is free of a bias of electric charge. When the compound is used as a surface treating agent or textile treating agent, the treated surface is kept electrically neutral because electric charges are offset by a weakly acidic amino group and a weakly basic carboxyl group. As a consequence, the adsorption to the surface by an electric charge is minimized. This ensures improved hydrophilic and antifouling properties.

In one aspect, the invention provides an amino acid-modified silane compound having the general formula (1):

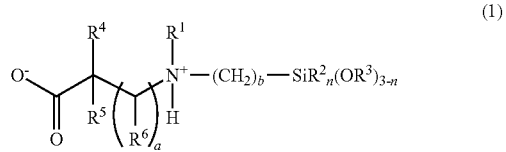

(1)

wherein $R^1$, $R^4$ and $R^5$ each are hydrogen or a substituted or unsubstituted, $C_1$-$C_{20}$ monovalent hydrocarbon group, $R^2$ and $R^3$ each are a substituted or unsubstituted, $C_1$-$C_{20}$ monovalent hydrocarbon group, $R^6$ is hydrogen, a substituted or unsubstituted, $C_1$-$C_{20}$ monovalent hydrocarbon group, or carboxyl group, a is 0 or 1, b is an integer of 1 to 10, and n is 0, 1 or 2.

Preferably in formula (1), $R^1$, $R^4$ and $R^5$ each are hydrogen, $R^6$ is hydrogen or carboxyl group, a is 1, b is 3, and n is 0, 1 or 2.

Typical of the silane compound of formula (1) are
N-(3-trimethoxysilylpropyl)-β-alanine,
N-(3-methyldimethoxysilylpropyl)-β-alanine,
N-(3-triethoxysilylpropyl)-β-alanine,
N-(3-methyldiethoxysilylpropyl)-β-alanine,
N-(3-trimethoxysilylpropyl)aspartic acid,
N-(3-methyldimethoxysilylpropyl)aspartic acid,
N-(3-triethoxysilylpropyl)aspartic acid, and
N-(3-methyldiethoxysilylpropyl)aspartic acid.

In another aspect, the invention provides a method for preparing the amino acid-modified silane compound of formula (1), comprising de-triorganosilylation reaction of a silyl-protected, amino acid-modified silane compound having the general formula (2):

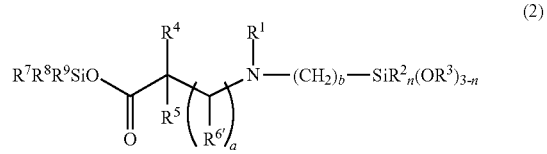

(2)

wherein $R^{1'}$ is $R^1$ or a triorganosilyl group of $R^{10}R^{11}R^{12}Si$—, $R^1$, $R^4$ and $R^5$ each are hydrogen or a substituted or unsubstituted, $C_1$-$C_{20}$ monovalent hydrocarbon group, $R^2$ and $R^3$ each are a substituted or unsubstituted, $C_1$-$C_{20}$ monovalent hydrocarbon group, $R^{6'}$ is hydrogen, a substituted or unsubstituted, $C_1$-$C_{20}$ monovalent hydrocarbon group, or silyl-protected carboxyl group, $R^7$, $R^8$, $R^9$, $R^{10}$, $R^{11}$ and $R^{12}$ each are a substituted or unsubstituted, $C_1$-$C_{20}$ monovalent hydrocarbon group, a is 0 or 1, b is an integer of 1 to 10, and n is 0, 1 or 2.

ADVANTAGEOUS EFFECTS OF INVENTION

When the amino acid-modified silane compound is used as a surface treating agent or textile treating agent, the treated surface is kept electrically neutral because electric charges are offset by a weakly acidic amino group and a weakly basic carboxyl group. As a consequence, the adsorption to the surface by an electric charge is minimized. This ensures improved hydrophilic and antifouling properties. The compound is thus useful as paint additives, adhesives, silane coupling agents, textile treating agents, surface treating agents, and the like.

DESCRIPTION OF EMBODIMENTS

Figure 1:
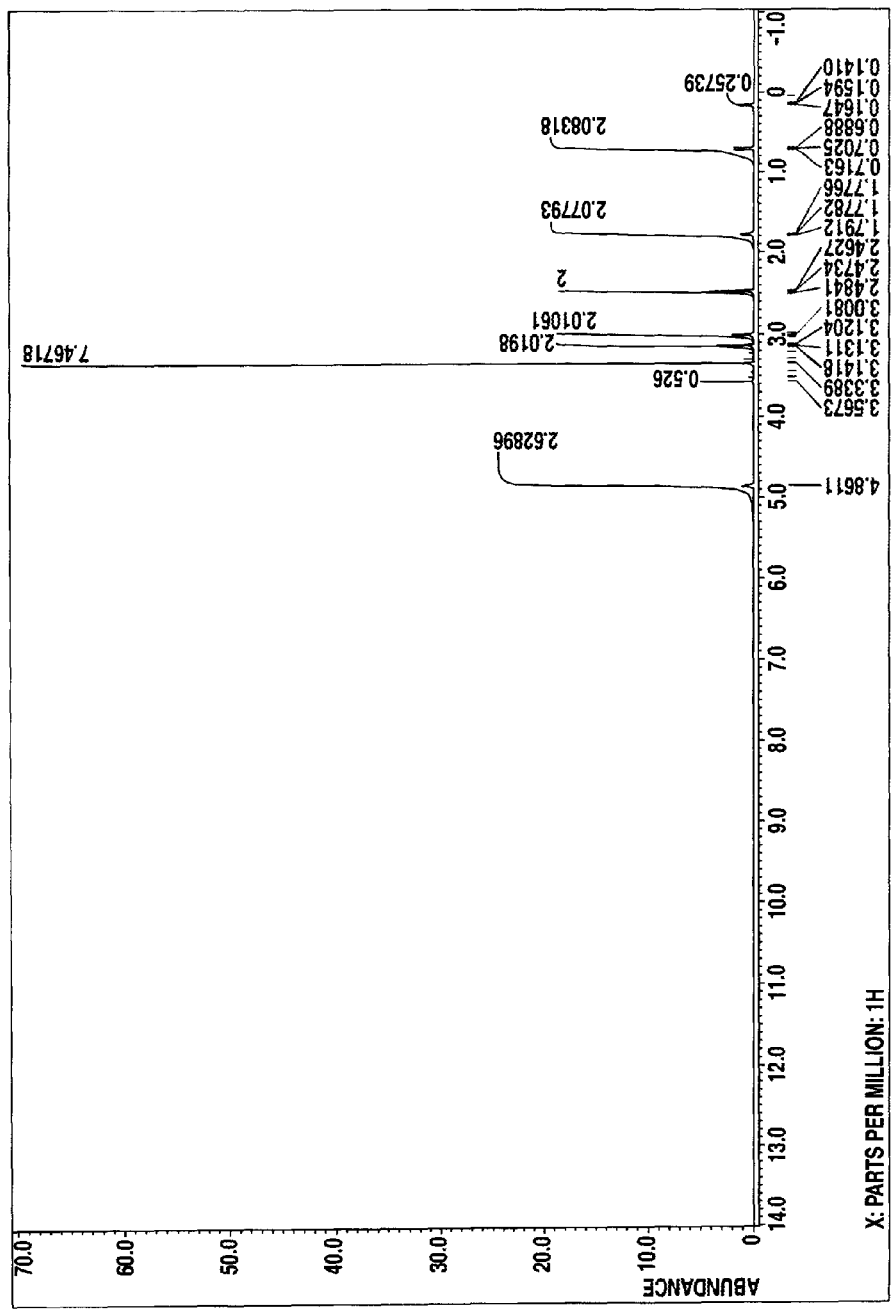
FIGS. 1 and 2 are $^1$H-NMR and IR spectra of N-(3-trimethoxysilylpropyl)-β-alanine obtained in Example 1, respectively.

As used herein, the notation (Cn-Cm) means a group containing from n to m carbon atoms per group.

One embodiment of the invention is an amino acid-modified silane compound having the general formula (1):

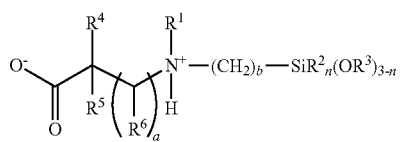

wherein $R^4$, $R^4$ and $R^5$ each are hydrogen or a substituted or unsubstituted, $C_1$-$C_{20}$ monovalent hydrocarbon group, $R^2$ and $R^3$ each are a substituted or unsubstituted, $C_1$-$C_{20}$ monovalent hydrocarbon group, $R^6$ is hydrogen, a substituted or unsubstituted, $C_1$-$C_{20}$ monovalent hydrocarbon group, or carboxyl group, a is 0 or 1, b is an integer of 1 to 10, and n is 0, 1 or 2.

When $R^1$, $R^4$, $R^5$, and $R^6$ are optionally substituted $C_1$-$C_{20}$ monovalent hydrocarbon groups, suitable hydrocarbon groups include straight, branched or cyclic alkyl groups, alkenyl groups, aryl groups, and aralkyl groups. Specifically exemplary groups include straight alkyl groups such as methyl, ethyl, propyl, butyl, pentyl, hexyl, heptyl, octyl, decyl, dodecyl, tetradecyl, hexadecyl, octadecyl and eicosyl; branched alkyl groups such as isopropyl, isobutyl, tert-butyl, thexyl, and 2-ethylhexyl; cyclic alkyl groups such as cyclopentyl and cyclohexyl; alkenyl groups such as vinyl, allyl, and propenyl; aryl groups such as phenyl and tolyl; and aralkyl groups such as benzyl. Inter alia, methyl and ethyl are preferred. Some or all hydrogen atoms on the hydrocarbon group may be substituted, while suitable substituent groups include alkoxy groups such as methoxy, ethoxy and (iso)propoxy, halogen atoms such as fluorine, chlorine, bromine and iodine, cyano groups, amino groups, $C_6$-$C_{18}$ aryl groups such as phenyl and tolyl, $C_7$-$C_{18}$ aralkyl groups such as benzyl and phenethyl, ester groups, ether groups, acyl groups, sulfide groups, alkylsilyl groups, and alkoxysilyl groups, and combinations of the foregoing.

$R^2$ and $R^3$ are optionally substituted $C_1$-$C_{20}$ monovalent hydrocarbon groups, examples of which are as illustrated above for $R^1$, $R^4$, $R^5$ and $R^6$, with methyl and ethyl being preferred.

The subscript a is 0 or 1, preferably 1, b is an integer of 1 to 10, preferably 3, and n is 0, 1 or 2.

Examples of the amino acid-modified silane compound having formula (1) include
N-(3-trimethoxysilylpropyl)-β-alanine,
N-(3-methyldimethoxysilylpropyl)-β-alanine,
N-(3-dimethylmethoxysilylpropyl)-β-alanine,
N-(3-triethoxysilylpropyl)-β-alanine,
N-(3-methyldiethoxysilylpropyl)-β-alanine,
N-(3-dimethylethoxysilylpropyl)-β-alanine,
N-(3-trimethoxysilylpropyl)-1-methyl-β-alanine,
N-(3-methyldimethoxysilylpropyl)-1-methyl-β-alanine,
N-(3-dimethylmethoxysilylpropyl)-1-methyl-β-alanine,
N-(3-triethoxysilylpropyl)-1-methyl-β-alanine,
N-(3-methyldiethoxysilylpropyl)-1-methyl-β-alanine,
N-(3-dimethylethoxysilylpropyl)-1-methyl-β-alanine,
N-(3-trimethoxysilylpropyl)aspartic acid,
N-(3-methyldimethoxysilylpropyl)aspartic acid,
N-(3-dimethylmethoxysilylpropyl)aspartic acid,
N-(3-triethoxysilylpropyl)aspartic acid,
N-(3-methyldiethoxysilylpropyl)aspartic acid,
N-(3-dimethylethoxysilylpropyl)aspartic acid,
N-(3-trimethoxysilylpropyl)-N-methyl-β-alanine,
N-(3-methyldimethoxysilylpropyl)-N-methyl-β-alanine,
N-(3-dimethylmethoxysilylpropyl)-N-methyl-β-alanine,
N-(3-triethoxysilylpropyl)-N-methyl-β-alanine,
N-(3-methyldiethoxysilylpropyl)-N-methyl-β-alanine,
N-(3-dimethylethoxysilylpropyl)-N-methyl-β-alanine,
N-(3-trimethoxysilylpropyl)-N-methyl-1-methyl-β-alanine,
N-(3-methyldimethoxysilylpropyl)-N-methyl-1-methyl-β-alanine,
N-(3-dimethylmethoxysilylpropyl)-N-methyl-1-methyl-β-alanine,
N-(3-triethoxysilylpropyl)-N-methyl-1-methyl-β-alanine,
N-(3-methyldiethoxysilylpropyl)-N-methyl-1-methyl-β-alanine,
N-(3-dimethylethoxysilylpropyl)-N-methyl-1-methyl-β-alanine,
N-(3-trimethoxysilylpropyl)-N-methylaspartic acid,
N-(3-methyldimethoxysilylpropyl)-N-methylaspartic acid,
N-(3-dimethylmethoxysilylpropyl)-N-methylaspartic acid,
N-(3-triethoxysilylpropyl)-N-methylaspartic acid,
N-(3-methyldiethoxysilylpropyl)-N-methylaspartic acid,
N-(3-dimethylethoxysilylpropyl)-N-methylaspartic acid,
N-(3-trimethoxysilylpropyl)-N-ethyl-β-alanine,
N-(3-methyldimethoxysilylpropyl)-N-ethyl-β-alanine,
N-(3-dimethylmethoxysilylpropyl)-N-ethyl-β-alanine, N-(3-triethoxysilylpropyl)-N-ethyl-β-alanine,
N-(3-methyldiethoxysilylpropyl)-N-ethyl-β-alanine,
N-(3-dimethylethoxysilylpropyl)-N-ethyl-β-alanine,
N-(3-trimethoxysilylpropyl)-N-ethyl-1-methyl-β-alanine,
N-(3-methyldimethoxysilylpropyl)-N-ethyl-1-methyl-β-alanine,
N-(3-dimethylmethoxysilylpropyl)-N-ethyl-1-methyl-β-alanine,
N-(3-triethoxysilylpropyl)-N-ethyl-1-methyl-β-alanine,
N-(3-methyldiethoxysilylpropyl)-N-ethyl-1-methyl-β-alanine,
N-(3-dimethylethoxysilylpropyl)-N-ethyl-1-methyl-β-alanine,
N-(3-trimethoxysilylpropyl)-N-ethylaspartic acid,
N-(3-methyldimethoxysilylpropyl)-N-ethylaspartic acid,
N-(3-dimethylmethoxysilylpropyl)-N-ethylaspartic acid,
N-(3-triethoxysilylpropyl)-N-ethylaspartic acid,
N-(3-methyldiethoxysilylpropyl)-N-ethylaspartic acid,
N-(3-dimethylethoxysilylpropyl)-N-ethylaspartic acid,
N-(3-trimethoxysilylpropyl)-N-phenyl-β-alanine,
N-(3-methyldimethoxysilylpropyl)-N-phenyl-β-alanine,
N-(3-dimethylmethoxysilylpropyl)-N-phenyl-β-alanine,
N-(3-triethoxysilylpropyl)-N-phenyl-β-alanine,
N-(3-methyldiethoxysilylpropyl)-N-phenyl-β-alanine,
N-(3-dimethylethoxysilylpropyl)-N-phenyl-β-alanine,
N-(3-trimethoxysilylpropyl)-N-phenyl-1-methyl-β-alanine,
N-(3-methyldimethoxysilylpropyl)-N-phenyl-1-methyl-β-alanine,
N-(3-dimethylmethoxysilylpropyl)-N-phenyl-1-methyl-β-alanine,
N-(3-triethoxysilylpropyl)-N-phenyl-1-methyl-β-alanine,
N-(3-methyldiethoxysilylpropyl)-N-phenyl-1-methyl-β-alanine,
N-(3-dimethylethoxysilylpropyl)-N-phenyl-1-methyl-β-alanine,
N-(3-trimethoxysilylpropyl)-N-phenylaspartic acid,
N-(3-methyldimethoxysilylpropyl)-N-phenylaspartic acid,
N-(3-dimethylmethoxysilylpropyl)-N-phenylaspartic acid,
N-(3-triethoxysilylpropyl)-N-phenylaspartic acid,
N-(3-methyldiethoxysilylpropyl)-N-phenylaspartic acid, and
N-(3-dimethylethoxysilylpropyl)-N-phenylaspartic acid.

Preference is given to
N-(3-trimethoxysilylpropyl)-β-alanine,
N-(3-methyldimethoxysilylpropyl)-β-alanine,
N-(3-triethoxysilylpropyl)-β-alanine,
N-(3-methyldiethoxysilylpropyl)-β-alanine,
N-(3-trimethoxysilylpropyl)aspartic acid,
N-(3-methyldimethoxysilylpropyl)aspartic acid,
N-(3-triethoxysilylpropyl)aspartic acid, and
N-(3-methyldiethoxysilylpropyl)aspartic acid.

Another embodiment of the invention is a method for preparing the amino acid-modified silane compound of formula (1). It may be prepared by de-triorganosilylation reaction of a silyl-protected, amino acid-modified silane compound having the general formula (2).

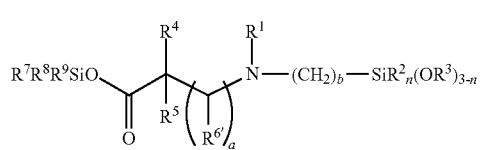

Herein $R^{1'}$ is $R^1$ or a triorganosilyl group of $R^{10}R^{11}R^{12}Si—$, $R^1$, $R^4$ and $R^5$ each are hydrogen or a substituted or unsubstituted, $C_1$-$C_{20}$ monovalent hydrocarbon group, $R^2$ and $R^3$ each are a substituted or unsubstituted, $C_1$-$C_{20}$ monovalent hydrocarbon group, $R^{6'}$ is hydrogen, a substituted or unsubstituted, $C_1$-$C_{20}$ monovalent hydrocarbon group, or silyl-protected carboxyl group, $R^7$, $R^8$, $R^9$, $R^{10}$, $R^{11}$ and $R^{12}$ each are a substituted or unsubstituted, $C_1$-$C_{20}$ monovalent hydrocarbon group, a is 0 or 1, b is an integer of 1 to 10, and n is 0, 1 or 2.

It is noted that those compounds of formula (2) wherein $R^{1'}$ is hydrogen are per se known. The compounds of formula (2) wherein $R^{1'}$ is triorganosilyl may be prepared by triorganosilylation of $R^{1'}$ on the compounds of formula (2) wherein $R^{1'}$ is hydrogen (see JP-A 2011-246391).

In formula (2), $R^1$, $R^2$, $R^3$, $R^4$, and $R^5$ are as exemplified above.

In formula (2), $R^{6'}$ may be an optionally substituted $C_1$-$C_{20}$ monovalent hydrocarbon group, examples of which are as exemplified for $R^1$ to $R^5$. $R^{6'}$ may also be a silyl-protected carboxyl group, examples of which include trimethylsiloxycarbonyl, ethyldimethylsiloxycarbonyl, diethylmethylsiloxycarbonyl, triethylsiloxycarbonyl, t-butyldimethylsiloxycarbonyl, triisopropylsiloxycarbonyl, thexyldimethylsiloxycarbonyl, octyldimethylsiloxycarbonyl, decyldimethylsiloxycarbonyl, octadecyldimethylsiloxycarbonyl, phenyldimethylsiloxycarbonyl, diphenylmethylsiloxycarbonyl, triphenylsiloxycarbonyl, and t-butyldiphenylsiloxycarbonyl.

Each of $R^7$, $R^8$, $R^9$, $R^{10}$, $R^{11}$ and $R^{12}$ is an optionally substituted $C_1$-$C_{20}$ monovalent hydrocarbon group, examples of which include straight alkyl groups such as methyl, ethyl, propyl, butyl, pentyl, hexyl, heptyl, octyl, decyl, dodecyl, tetradecyl, hexadecyl, octadecyl, and eicosyl; branched alkyl groups such as isopropyl, isobutyl, tert-butyl, thexyl, and 2-ethylhexyl; cyclic alkyl groups such as cyclopentyl and cyclohexyl; alkenyl groups such as vinyl, allyl and propenyl; aryl groups such as phenyl and tolyl; and aralkyl groups such as benzyl. Suitable substituted monovalent hydrocarbon groups are as exemplified for $R^1$ and $R^4$ to $R^6$. Inter alia, methyl, ethyl, isopropyl, and t-butyl are preferred. Examples of the triorganosilyl group of $R^7R^8R^9Si—$ or $R^{10}R^{11}R^{12}Si—$ include trimethylsilyl, ethyldimethylsilyl, diethylmethylsilyl, triethylsilyl, t-butyldimethylsilyl, triisopropylsilyl, thexyldimethylsilyl, octyldimethylsilyl, decyldimethylsilyl, octadecyldimethylsilyl, phenyldimethylsilyl, diphenylmethylsilyl, triphenylsilyl, and t-butyldiphenylsilyl. Inter alia, trimethylsilyl, triethylsilyl, t-butyldimethylsilyl, and triisopropylsilyl are preferred.

Examples of the silyl-protected, amino acid-modified silane compound having formula (2) include
N-(2-trimethylsiloxycarbonyl)ethyl-3-aminopropyltrimethoxy-silane,
N-(2-trimethylsiloxycarbonyl)ethyl-3-aminopropylmethyldimethoxysilane,
N-(2-trimethylsiloxycarbonyl)ethyl-3-aminopropyldimethyl-methoxysilane,
N-(2-trimethylsiloxycarbonyl)ethyl-3-aminopropyltriethoxy-silane,
N-(2-trimethylsiloxycarbonyl)ethyl-3-aminopropylmethyldiethoxysilane,
N-(2-trimethylsiloxycarbonyl)ethyl-3-aminopropyldimethyl-ethoxysilane,
N-(2-trimethylsiloxycarbonyl-2-methyl)ethyl-3-aminopropyl-trimethoxysilane, N-(2-trimethylsiloxycarbonyl-2-methyl)ethyl-3-aminopropyl-methyldimethoxysilane,
N-(2-trimethylsiloxycarbonyl-2-methyl)ethyl-3-aminopropyl-dimethylmethoxysilane,
N-(2-trimethylsiloxycarbonyl-2-methyl)ethyl-3-aminopropyl-triethoxysilane,
N-(2-trimethylsiloxycarbonyl-2-methyl)ethyl-3-aminopropyl-methyldiethoxysilane,
N-(2-trimethylsiloxycarbonyl-2-methyl)ethyl-3-aminopropyl-dimethylethoxysilane,
N-(1,2-bistrimethylsiloxycarbonyl)ethyl-3-aminopropyl-trimethoxysilane,
N-(1,2-bistrimethylsiloxycarbonyl)ethyl-3-aminopropyl-methyldimethoxysilane,
N-(1,2-bistrimethylsiloxycarbonyl)ethyl-3-aminopropyl-dimethylmethoxysilane,
N-(1,2-bistrimethylsiloxycarbonyl)ethyl-3-aminopropyl-triethoxysilane,
N-(1,2-bistrimethylsiloxycarbonyl)ethyl-3-aminopropyl-methyldiethoxysilane,
N-(1,2-bistrimethylsiloxycarbonyl)ethyl-3-aminopropyl-dimethylethoxysilane,
N-(2-trimethylsiloxycarbonyl)ethyl-N-methyl-3-aminopropyl-trimethoxysilane,
N-(2-trimethylsiloxycarbonyl)ethyl-N-methyl-3-aminopropyl-methyldimethoxysilane,
N-(2-trimethylsiloxycarbonyl)ethyl-N-methyl-3-aminopropyl-dimethylmethoxysilane,
N-(2-trimethylsiloxycarbonyl)ethyl-N-methyl-3-aminopropyl-triethoxysilane,
N-(2-trimethylsiloxycarbonyl)ethyl-N-methyl-3-aminopropyl-methyldiethoxysilane,
N-(2-trimethylsiloxycarbonyl)ethyl-N-methyl-3-aminopropyl-dimethylethoxysilane,
N-(2-trimethylsiloxycarbonyl-2-methyl)ethyl-N-methyl-3-aminopropyltrimethoxysilane,
N-(2-trimethylsiloxycarbonyl-2-methyl)ethyl-N-methyl-3-aminopropylmethyldimethoxysilane,
N-(2-trimethylsiloxycarbonyl-2-methyl)ethyl-N-methyl-3-aminopropyldimethylmethoxysilane,
N-(2-trimethylsiloxycarbonyl-2-methyl)ethyl-N-methyl-3-aminopropyltriethoxysilane,
N-(2-trimethylsiloxycarbonyl-2-methyl)ethyl-N-methyl-3-aminopropylmethyldiethoxysilane,
N-(2-trimethylsiloxycarbonyl-2-methyl)ethyl-N-methyl-3-aminopropyldimethylethoxysilane,
N-(1,2-bistrimethylsiloxycarbonyl)ethyl-N-methyl-3-aminopropyltrimethoxysilane,
N-(1,2-bistrimethylsiloxycarbonyl)ethyl-N-methyl-3-aminopropylmethyldimethoxysilane,
N-(1,2-bistrimethylsiloxycarbonyl)ethyl-N-methyl-3-aminopropyldimethylmethoxysilane,
N-(1,2-bistrimethylsiloxycarbonyl)ethyl-N-methyl-3-aminopropyltriethoxysilane,
N-(1,2-bistrimethylsiloxycarbonyl)ethyl-N-methyl-3-aminopropylmethyldiethoxysilane,
N-(1,2-bistrimethylsiloxycarbonyl)ethyl-N-methyl-3-aminopropyldimethylethoxysilane,
N-(2-trimethylsiloxycarbonyl)ethyl-N-ethyl-3-aminopropyl-trimethoxysilane,
N-(2-trimethylsiloxycarbonyl)ethyl-N-ethyl-3-aminopropyl-methyldimethoxysilane,
N-(2-trimethylsiloxycarbonyl)ethyl-N-ethyl-3-aminopropyl-dimethylmethoxysilane,
N-(2-trimethylsiloxycarbonyl)ethyl-N-ethyl-3-aminopropyl-triethoxysilane,
N-(2-trimethylsiloxycarbonyl)ethyl-N-ethyl-3-aminopropyl-methyldiethoxysilane,
N-(2-trimethylsiloxycarbonyl)ethyl-N-ethyl-3-aminopropyl-dimethylethoxysilane,
N-(2-trimethylsiloxycarbonyl-2-methyl)ethyl-N-ethyl-3-aminopropyltrimethoxysilane,
N-(2-trimethylsiloxycarbonyl-2-methyl)ethyl-N-ethyl-3-aminopropylmethyldimethoxysilane,
N-(2-trimethylsiloxycarbonyl-2-methyl)ethyl-N-ethyl-3-aminopropyldimethylmethoxysilane,
N-(2-trimethylsiloxycarbonyl-2-methyl)ethyl-N-ethyl-3-aminopropyltriethoxysilane,
N-(2-trimethylsiloxycarbonyl-2-methyl)ethyl-N-ethyl-3-aminopropylmethyldiethoxysilane,
N-(2-trimethylsiloxycarbonyl-2-methyl)ethyl-N-ethyl-3-aminopropyldimethylethoxysilane,
N-(1,2-bistrimethylsiloxycarbonyl)ethyl-N-ethyl-3-aminopropyltrimethoxysilane,
N-(1,2-bistrimethylsiloxycarbonyl)ethyl-N-ethyl-3-aminopropylmethyldimethoxysilane,
N-(1,2-bistrimethylsiloxycarbonyl)ethyl-N-ethyl-3-aminopropyldimethylmethoxysilane,
N-(1,2-bistrimethylsiloxycarbonyl)ethyl-N-ethyl-3-aminopropyltriethoxysilane,
N-(1,2-bistrimethylsiloxycarbonyl)ethyl-N-ethyl-3-aminopropylmethyldiethoxysilane,
N-(1,2-bistrimethylsiloxycarbonyl)ethyl-N-ethyl-3-aminopropyldimethylethoxysilane,
N-(2-trimethylsiloxycarbonyl)ethyl-N-phenyl-3-aminopropyl-trimethoxysilane,
N-(2-trimethylsiloxycarbonyl)ethyl-N-phenyl-3-aminopropyl-methyldimethoxysilane,
N-(2-trimethylsiloxycarbonyl)ethyl-N-phenyl-3-aminopropyl-dimethylmethoxysilane,
N-(2-trimethylsiloxycarbonyl)ethyl-N-phenyl-3-aminopropyl-triethoxysilane,
N-(2-trimethylsiloxycarbonyl)ethyl-N-phenyl-3-aminopropyl-methyldiethoxysilane,
N-(2-trimethylsiloxycarbonyl)ethyl-N-phenyl-3-aminopropyl-dimethylethoxysilane,
N-(2-trimethylsiloxycarbonyl-2-methyl)ethyl-N-phenyl-3-aminopropyltrimethoxysilane,
N-(2-trimethylsiloxycarbonyl-2-methyl)ethyl-N-phenyl-3-aminopropylmethyldimethoxysilane,
N-(2-trimethylsiloxycarbonyl-2-methyl)ethyl-N-phenyl-3-aminopropyldimethylmethoxysilane,
N-(2-trimethylsiloxycarbonyl-2-methyl)ethyl-N-phenyl-3-aminopropyltriethoxysilane,
N-(2-trimethylsiloxycarbonyl-2-methyl)ethyl-N-phenyl-3-aminopropylmethyldiethoxysilane,
N-(2-trimethylsiloxycarbonyl-2-methyl)ethyl-N-phenyl-3-aminopropyldimethylethoxysilane,
N-(1,2-bistrimethylsiloxycarbonyl)ethyl-N-phenyl-3-aminopropyltrimethoxysilane,
N-(1,2-bistrimethylsiloxycarbonyl)ethyl-N-phenyl-3-aminopropylmethyldimethoxysilane,
N-(1,2-bistrimethylsiloxycarbonyl)ethyl-N-phenyl-3-aminopropyldimethylmethoxysilane,
N-(1,2-bistrimethylsiloxycarbonyl)ethyl-N-phenyl-3-aminopropyltriethoxysilane,
N-(1,2-bistrimethylsiloxycarbonyl)ethyl-N-phenyl-3-aminopropylmethyldiethoxysilane,
N-(1,2-bistrimethylsiloxycarbonyl)ethyl-N-phenyl-3-aminopropyldimethylethoxysilane,
N-(2-trimethylsiloxycarbonyl)ethyl-N-trimethylsilyl-3-aminopropyltrimethoxysilane, N-(2-trimethylsiloxycarbonyl)ethyl-N-trimethylsilyl-3-aminopropylmethyldimethoxysilane,
N-(2-trimethylsiloxycarbonyl)ethyl-N-trimethylsilyl-3-aminopropyldimethylmethoxysilane,
N-(2-trimethylsiloxycarbonyl)ethyl-N-trimethylsilyl-3-aminopropyltriethoxysilane,
N-(2-trimethylsiloxycarbonyl)ethyl-N-trimethylsilyl-3-aminopropylmethyldiethoxysilane,
N-(2-trimethylsiloxycarbonyl)ethyl-N-trimethylsilyl-3-aminopropyldimethylethoxysilane,
N-(2-trimethylsiloxycarbonyl-2-methyl)ethyl-N-trimethylsilyl-3-aminopropyltrimethoxysilane,
N-(2-trimethylsiloxycarbonyl-2-methyl)ethyl-N-trimethylsilyl-3-aminopropylmethyldimethoxysilane,
N-(2-trimethylsiloxycarbonyl-2-methyl)ethyl-N-trimethylsilyl-3-aminopropyldimethylmethoxysilane,
N-(2-trimethylsiloxycarbonyl-2-methyl)ethyl-N-trimethylsilyl-3-aminopropyltriethoxysilane,
N-(2-trimethylsiloxycarbonyl-2-methyl)ethyl-N-trimethylsilyl-3-aminopropylmethyldiethoxysilane,
N-(2-trimethylsiloxycarbonyl-2-methyl)ethyl-N-trimethylsilyl-3-aminopropyldimethylethoxysilane,
N-(1,2-bistrimethylsiloxycarbonyl)ethyl-N-trimethylsilyl-3-aminopropyltrimethoxysilane,
N-(1,2-bistrimethylsiloxycarbonyl)ethyl-N-trimethylsilyl-3-aminopropylmethyldimethoxysilane,
N-(1,2-bistrimethylsiloxycarbonyl)ethyl-N-trimethylsilyl-3-aminopropyldimethylmethoxysilane,
N-(1,2-bistrimethylsiloxycarbonyl)ethyl-N-trimethylsilyl-3-aminopropyltriethoxysilane,
N-(1,2-bistrimethylsiloxycarbonyl)ethyl-N-trimethylsilyl-3-aminopropylmethyldiethoxysilane,
N-(1,2-bistrimethylsiloxycarbonyl)ethyl-N-trimethylsilyl-3-aminopropyldimethylethoxysilane,
N-(2-triethylsiloxycarbonyl)ethyl-3-aminopropyltrimethoxy-silane,
N-(2-triethylsiloxycarbonyl)ethyl-3-aminopropylmethyl-dimethoxysilane,
N-(2-triethylsiloxycarbonyl)ethyl-3-aminopropyldimethylmethoxysilane,
N-(2-triethylsiloxycarbonyl)ethyl-3-aminopropyltriethoxysilane,
N-(2-triethylsiloxycarbonyl)ethyl-3-aminopropylmethyl-diethoxysilane,
N-(2-triethylsiloxycarbonyl)ethyl-3-aminopropyldimethylethoxysilane,
N-(2-triethylsiloxycarbonyl-2-methyl)ethyl-3-aminopropyltrimethoxysilane,
N-(2-triethylsiloxycarbonyl-2-methyl)ethyl-3-aminopropylmethyldimethoxysilane,
N-(2-triethylsiloxycarbonyl-2-methyl)ethyl-3-aminopropyldimethylmethoxysilane,
N-(2-triethylsiloxycarbonyl-2-methyl)ethyl-3-aminopropyltriethoxysilane,
N-(2-triethylsiloxycarbonyl-2-methyl)ethyl-3-aminopropylmethyldiethoxysilane,
N-(2-triethylsiloxycarbonyl-2-methyl)ethyl-3-aminopropyldimethylethoxysilane,
N-(1,2-bistriethylsiloxycarbonyl)ethyl-3-aminopropyltrimethoxysilane,
N-(1,2-bistriethylsiloxycarbonyl)ethyl-3-aminopropylmethyldimethoxysilane,
N-(1,2-bistriethylsiloxycarbonyl)ethyl-3-aminopropyl-dimethylmethoxysilane,
N-(1,2-bistriethylsiloxycarbonyl)ethyl-3-aminopropyl-triethoxysilane,
N-(1,2-bistriethylsiloxycarbonyl)ethyl-3-aminopropyl-methyldiethoxysilane,
N-(1,2-bistriethylsiloxycarbonyl)ethyl-3-aminopropyl-dimethylethoxysilane,
N-(2-triethylsiloxycarbonyl)ethyl-N-methyl-3-aminopropyl-trimethoxysilane,
N-(2-triethylsiloxycarbonyl)ethyl-N-methyl-3-aminopropyl-methyldimethoxysilane,
N-(2-triethylsiloxycarbonyl)ethyl-N-methyl-3-aminopropyl-dimethylmethoxysilane,
N-(2-triethylsiloxycarbonyl)ethyl-N-methyl-3-aminopropyl-triethoxysilane,
N-(2-triethylsiloxycarbonyl)ethyl-N-methyl-3-aminopropyl-methyldiethoxysilane,
N-(2-triethylsiloxycarbonyl)ethyl-N-methyl-3-aminopropyl-dimethylethoxysilane,
N-(2-triethylsiloxycarbonyl-2-methyl)ethyl-N-methyl-3-aminopropyltrimethoxysilane,
N-(2-triethylsiloxycarbonyl-2-methyl)ethyl-N-methyl-3-aminopropylmethyldimethoxysilane,
N-(2-triethylsiloxycarbonyl-2-methyl)ethyl-N-methyl-3-aminopropyldimethylmethoxysilane,
N-(2-triethylsiloxycarbonyl-2-methyl)ethyl-N-methyl-3-aminopropyltriethoxysilane,
N-(2-triethylsiloxycarbonyl-2-methyl)ethyl-N-methyl-3-aminopropylmethyldiethoxysilane,
N-(2-triethylsiloxycarbonyl-2-methyl)ethyl-N-methyl-3-aminopropyldimethylethoxysilane,
N-(1,2-bistriethylsiloxycarbonyl)ethyl-N-methyl-3-aminopropyltrimethoxysilane,
N-(1,2-bistriethylsiloxycarbonyl)ethyl-N-methyl-3-aminopropylmethyldimethoxysilane,
N-(1,2-bistriethylsiloxycarbonyl)ethyl-N-methyl-3-aminopropyldimethylmethoxysilane,
N-(1,2-bistriethylsiloxycarbonyl)ethyl-N-methyl-3-aminopropyltriethoxysilane,
N-(1,2-bistriethylsiloxycarbonyl)ethyl-N-methyl-3-aminopropylmethyldiethoxysilane,
N-(1,2-bistriethylsiloxycarbonyl)ethyl-N-methyl-3-aminopropyldimethylethoxysilane,
N-(2-triethylsiloxycarbonyl)ethyl-N-ethyl-3-aminopropyl-trimethoxysilane,
N-(2-triethylsiloxycarbonyl)ethyl-N-ethyl-3-aminopropyl-methyldimethoxysilane,
N-(2-triethylsiloxycarbonyl)ethyl-N-ethyl-3-aminopropyl-dimethylmethoxysilane,
N-(2-triethylsiloxycarbonyl)ethyl-N-ethyl-3-aminopropyl-triethoxysilane,
N-(2-triethylsiloxycarbonyl)ethyl-N-ethyl-3-aminopropyl-methyldiethoxysilane,
N-(2-triethylsiloxycarbonyl)ethyl-N-ethyl-3-aminopropyl-dimethylethoxysilane,
N-(2-triethylsiloxycarbonyl-2-methyl)ethyl-N-ethyl-3-aminopropyltrimethoxysilane,
N-(2-triethylsiloxycarbonyl-2-methyl)ethyl-N-ethyl-3-aminopropylmethyldimethoxysilane,
N-(2-triethylsiloxycarbonyl-2-methyl)ethyl-N-ethyl-3-aminopropyldimethylmethoxysilane,
N-(2-triethylsiloxycarbonyl-2-methyl)ethyl-N-ethyl-3-aminopropyltriethoxysilane,
N-(2-triethylsiloxycarbonyl-2-methyl)ethyl-N-ethyl-3-aminopropylmethyldiethoxysilane,
N-(2-triethylsiloxycarbonyl-2-methyl)ethyl-N-ethyl-3-aminopropyldimethylethoxysilane,
N-(1,2-bistriethylsiloxycarbonyl)ethyl-N-ethyl-3-aminopropyl-trimethoxysilane, N-(1,2-bistriethylsiloxycarbonyl)ethyl-N-ethyl-3-aminopropyl-methyldimethoxysilane,
N-(1,2-bistriethylsiloxycarbonyl)ethyl-N-ethyl-3-aminopropyl-dimethylmethoxysilane,
N-(1,2-bistriethylsiloxycarbonyl)ethyl-N-ethyl-3-aminopropyl-triethoxysilane,
N-(1,2-bistriethylsiloxycarbonyl)ethyl-N-ethyl-3-aminopropyl-methyldiethoxysilane,
N-(1,2-bistriethylsiloxycarbonyl)ethyl-N-ethyl-3-aminopropyl-dimethylethoxysilane,
N-(2-triethylsiloxycarbonyl)ethyl-N-phenyl-3-aminopropyl-trimethoxysilane,
N-(2-triethylsiloxycarbonyl)ethyl-N-phenyl-3-aminopropyl-methyldimethoxysilane,
N-(2-triethylsiloxycarbonyl)ethyl-N-phenyl-3-aminopropyl-dimethylmethoxysilane,
N-(2-triethylsiloxycarbonyl)ethyl-N-phenyl-3-aminopropyl-triethoxysilane,
N-(2-triethylsiloxycarbonyl)ethyl-N-phenyl-3-aminopropyl-methyldiethoxysilane,
N-(2-triethylsiloxycarbonyl)ethyl-N-phenyl-3-aminopropyl-dimethylethoxysilane,
N-(2-triethylsiloxycarbonyl-2-methyl)ethyl-N-phenyl-3-aminopropyltrimethoxysilane,
N-(2-triethylsiloxycarbonyl-2-methyl)ethyl-N-phenyl-3-aminopropylmethyldimethoxysilane,
N-(2-triethylsiloxycarbonyl-2-methyl)ethyl-N-phenyl-3-aminopropyldimethylmethoxysilane,
N-(2-triethylsiloxycarbonyl-2-methyl)ethyl-N-phenyl-3-aminopropyltriethoxysilane,
N-(2-triethylsiloxycarbonyl-2-methyl)ethyl-N-phenyl-3-aminopropylmethyldiethoxysilane,
N-(2-triethylsiloxycarbonyl-2-methyl)ethyl-N-phenyl-3-aminopropyldimethylethoxysilane,
N-(1,2-bistriethylsiloxycarbonyl)ethyl-N-phenyl-3-aminopropyltrimethoxysilane,
N-(1,2-bistriethylsiloxycarbonyl)ethyl-N-phenyl-3-aminopropylmethyldimethoxysilane,
N-(1,2-bistriethylsiloxycarbonyl)ethyl-N-phenyl-3-aminopropyldimethylmethoxysilane,
N-(1,2-bistriethylsiloxycarbonyl)ethyl-N-phenyl-3-aminopropyltriethoxysilane,
N-(1,2-bistriethylsiloxycarbonyl)ethyl-N-phenyl-3-aminopropylmethyldiethoxysilane,
N-(1,2-bistriethylsiloxycarbonyl)ethyl-N-phenyl-3-aminopropyldimethylethoxysilane,
N-(2-triethylsiloxycarbonyl)ethyl-N-trimethylsilyl-3-aminopropyltrimethoxysilane,
N-(2-triethylsiloxycarbonyl)ethyl-N-trimethylsilyl-3-aminopropylmethyldimethoxysilane,
N-(2-triethylsiloxycarbonyl)ethyl-N-trimethylsilyl-3-aminopropyldimethylmethoxysilane,
N-(2-triethylsiloxycarbonyl)ethyl-N-trimethylsilyl-3-aminopropyltriethoxysilane,
N-(2-triethylsiloxycarbonyl)ethyl-N-trimethylsilyl-3-aminopropylmethyldiethoxysilane,
N-(2-triethylsiloxycarbonyl)ethyl-N-trimethylsilyl-3-aminopropyldimethylethoxysilane,
N-(2-triethylsiloxycarbonyl-2-methyl)ethyl-N-trimethylsilyl-3-aminopropyltrimethoxysilane,
N-(2-triethylsiloxycarbonyl-2-methyl)ethyl-N-trimethylsilyl-3-aminopropylmethyldimethoxysilane,
N-(2-triethylsiloxycarbonyl-2-methyl)ethyl-N-trimethylsilyl-3-aminopropyldimethylmethoxysilane,
N-(2-triethylsiloxycarbonyl-2-methyl)ethyl-N-trimethylsilyl-3-aminopropyltriethoxysilane,
N-(2-triethylsiloxycarbonyl-2-methyl)ethyl-N-trimethylsilyl-3-aminopropylmethyldiethoxysilane,
N-(2-triethylsiloxycarbonyl-2-methyl)ethyl-N-trimethylsilyl-3-aminopropyldimethylethoxysilane,
N-(1,2-bistriethylsiloxycarbonyl)ethyl-N-trimethylsilyl-3-aminopropyltrimethoxysilane,
N-(1,2-bistriethylsiloxycarbonyl)ethyl-N-trimethylsilyl-3-aminopropylmethyldimethoxysilane,
N-(1,2-bistriethylsiloxycarbonyl)ethyl-N-trimethylsilyl-3-aminopropyldimethylmethoxysilane,
N-(1,2-bistriethylsiloxycarbonyl)ethyl-N-trimethylsilyl-3-aminopropyltriethoxysilane,
N-(1,2-bistriethylsiloxycarbonyl)ethyl-N-trimethylsilyl-3-aminopropylmethyldiethoxysilane,
N-(1,2-bistriethylsiloxycarbonyl)ethyl-N-trimethylsilyl-3-aminopropyldimethylethoxysilane,
N-(2-t-butyldimethylsiloxycarbonyl)ethyl-3-aminopropyl-trimethoxysilane,
N-(2-t-butyldimethylsiloxycarbonyl)ethyl-3-aminopropyl-methyldimethoxysilane,
N-(2-t-butyldimethylsiloxycarbonyl)ethyl-3-aminopropyl-dimethylmethoxysilane,
N-(2-t-butyldimethylsiloxycarbonyl)ethyl-3-aminopropyl-triethoxysilane,
N-(2-t-butyldimethylsiloxycarbonyl)ethyl-3-aminopropyl-methyldiethoxysilane,
N-(2-t-butyldimethylsiloxycarbonyl)ethyl-3-aminopropyl-dimethylethoxysilane,
N-(2-t-butyldimethylsiloxycarbonyl-2-methyl)ethyl-3-aminopropyltrimethoxysilane,
N-(2-t-butyldimethylsiloxycarbonyl-2-methyl)ethyl-3-aminopropylmethyldimethoxysilane,
N-(2-t-butyldimethylsiloxycarbonyl-2-methyl)ethyl-3-aminopropyldimethylmethoxysilane,
N-(2-t-butyldimethylsiloxycarbonyl-2-methyl)ethyl-3-aminopropyltriethoxysilane,
N-(2-t-butyldimethylsiloxycarbonyl-2-methyl)ethyl-3-aminopropylmethyldiethoxysilane,
N-(2-t-butyldimethylsiloxycarbonyl-2-methyl)ethyl-3-aminopropyldimethylethoxysilane,
N-(1,2-bis-t-butyldimethylsiloxycarbonyl)ethyl-3-aminopropyl-trimethoxysilane,
N-(1,2-bis-t-butyldimethylsiloxycarbonyl)ethyl-3-aminopropyl-methyldimethoxysilane,
N-(1,2-bis-t-butyldimethylsiloxycarbonyl)ethyl-3-aminopropyl-dimethylmethoxysilane,
N-(1,2-bis-t-butyldimethylsiloxycarbonyl)ethyl-3-aminopropyl-triethoxysilane,
N-(1,2-bis-t-butyldimethylsiloxycarbonyl)ethyl-3-aminopropyl-methyldiethoxysilane,
N-(1,2-bis-t-butyldimethylsiloxycarbonyl)ethyl-3-aminopropyl-dimethylethoxysilane,
N-(2-t-butyldimethylsiloxycarbonyl)ethyl-N-methyl-3-aminopropyltrimethoxysilane,
N-(2-t-butyldimethylsiloxycarbonyl)ethyl-N-methyl-3-aminopropylmethyldimethoxysilane,
N-(2-t-butyldimethylsiloxycarbonyl)ethyl-N-methyl-3-aminopropyldimethylmethoxysilane,
N-(2-t-butyldimethylsiloxycarbonyl)ethyl-N-methyl-3-aminopropyltriethoxysilane,
N-(2-t-butyldimethylsiloxycarbonyl)ethyl-N-methyl-3-aminopropylmethyldiethoxysilane,
N-(2-t-butyldimethylsiloxycarbonyl)ethyl-N-methyl-3-aminopropyldimethylethoxysilane,
N-(2-t-butyldimethylsiloxycarbonyl-2-methyl)ethyl-N-methyl-3-aminopropyltrimethoxysilane, N-(2-t-butyldimethylsiloxycarbonyl-2-methyl)ethyl-N-methyl-3-aminopropylmethyldimethoxysilane,
N-(2-t-butyldimethylsiloxycarbonyl-2-methyl)ethyl-N-methyl-3-aminopropyldimethylmethoxysilane,
N-(2-t-butyldimethylsiloxycarbonyl-2-methyl)ethyl-N-methyl-3-aminopropyltriethoxysilane,
N-(2-t-butyldimethylsiloxycarbonyl-2-methyl)ethyl-N-methyl-3-aminopropylmethyldiethoxysilane,
N-(2-t-butyldimethylsiloxycarbonyl-2-methyl)ethyl-N-methyl-3-aminopropyldimethylethoxysilane,
N-(1,2-bis-t-butyldimethylsiloxycarbonyl)ethyl-N-methyl-3-aminopropyltrimethoxysilane,
N-(1,2-bis-t-butyldimethylsiloxycarbonyl)ethyl-N-methyl-3-aminopropylmethyldimethoxysilane,
N-(1,2-bis-t-butyldimethylsiloxycarbonyl)ethyl-N-methyl-3-aminopropyldimethylmethoxysilane,
N-(1,2-bis-t-butyldimethylsiloxycarbonyl)ethyl-N-methyl-3-aminopropyltriethoxysilane,
N-(1,2-bis-t-butyldimethylsiloxycarbonyl)ethyl-N-methyl-3-aminopropylmethyldiethoxysilane,
N-(1,2-bis-t-butyldimethylsiloxycarbonyl)ethyl-N-methyl-3-aminopropyldimethylethoxysilane,
N-(2-t-butyldimethylsiloxycarbonyl)ethyl-N-ethyl-3-aminopropyltrimethoxysilane,
N-(2-t-butyldimethylsiloxycarbonyl)ethyl-N-ethyl-3-aminopropylmethyldimethoxysilane,
N-(2-t-butyldimethylsiloxycarbonyl)ethyl-N-ethyl-3-aminopropyldimethylmethoxysilane,
N-(2-t-butyldimethylsiloxycarbonyl)ethyl-N-ethyl-3-aminopropyltriethoxysilane,
N-(2-t-butyldimethylsiloxycarbonyl)ethyl-N-ethyl-3-aminopropylmethyldiethoxysilane,
N-(2-t-butyldimethylsiloxycarbonyl)ethyl-N-ethyl-3-aminopropyldimethylethoxysilane,
N-(2-t-butyldimethylsiloxycarbonyl-2-methyl)ethyl-N-ethyl-3-aminopropyltrimethoxysilane,
N-(2-t-butyldimethylsiloxycarbonyl-2-methyl)ethyl-N-ethyl-3-aminopropylmethyldimethoxysilane,
N-(2-t-butyldimethylsiloxycarbonyl-2-methyl)ethyl-N-ethyl-3-aminopropyldimethylmethoxysilane,
N-(2-t-butyldimethylsiloxycarbonyl-2-methyl)ethyl-N-ethyl-3-aminopropyltriethoxysilane,
N-(2-t-butyldimethylsiloxycarbonyl-2-methyl)ethyl-N-ethyl-3-aminopropylmethyldiethoxysilane,
N-(2-t-butyldimethylsiloxycarbonyl-2-methyl)ethyl-N-ethyl-3-aminopropyldimethylethoxysilane,
N-(1,2-bis-t-butyldimethylsiloxycarbonyl)ethyl-N-ethyl-3-aminopropyltrimethoxysilane,
N-(1,2-bis-t-butyldimethylsiloxycarbonyl)ethyl-N-ethyl-3-aminopropylmethyldimethoxysilane,
N-(1,2-bis-t-butyldimethylsiloxycarbonyl)ethyl-N-ethyl-3-aminopropyldimethylmethoxysilane,
N-(1,2-bis-t-butyldimethylsiloxycarbonyl)ethyl-N-ethyl-3-aminopropyltriethoxysilane,
N-(1,2-bis-t-butyldimethylsiloxycarbonyl)ethyl-N-ethyl-3-aminopropylmethyldiethoxysilane,
N-(1,2-bis-t-butyldimethylsiloxycarbonyl)ethyl-N-ethyl-3-aminopropyldimethylethoxysilane,
N-(2-t-butyldimethylsiloxycarbonyl)ethyl-N-phenyl-3-aminopropyltrimethoxysilane,
N-(2-t-butyldimethylsiloxycarbonyl)ethyl-N-phenyl-3-aminopropylmethyldimethoxysilane,
N-(2-t-butyldimethylsiloxycarbonyl)ethyl-N-phenyl-3-aminopropyldimethylmethoxysilane,
N-(2-t-butyldimethylsiloxycarbonyl)ethyl-N-phenyl-3-aminopropyltriethoxysilane,
N-(2-t-butyldimethylsiloxycarbonyl)ethyl-N-phenyl-3-aminopropylmethyldiethoxysilane,
N-(2-t-butyldimethylsiloxycarbonyl)ethyl-N-phenyl-3-aminopropyldimethylethoxysilane,
N-(2-t-butyldimethylsiloxycarbonyl-2-methyl)ethyl-N-phenyl-3-aminopropyltrimethoxysilane,
N-(2-t-butyldimethylsiloxycarbonyl-2-methyl)ethyl-N-phenyl-3-aminopropylmethyldimethoxysilane,
N-(2-t-butyldimethylsiloxycarbonyl-2-methyl)ethyl-N-phenyl-3-aminopropyldimethylmethoxysilane,
N-(2-t-butyldimethylsiloxycarbonyl-2-methyl)ethyl-N-phenyl-3-aminopropyltriethoxysilane,
N-(2-t-butyldimethylsiloxycarbonyl-2-methyl)ethyl-N-phenyl-3-aminopropylmethyldiethoxysilane,
N-(2-t-butyldimethylsiloxycarbonyl-2-methyl)ethyl-N-phenyl-3-aminopropyldimethylethoxysilane,
N-(1,2-bis-t-butyldimethylsiloxycarbonyl)ethyl-N-phenyl-3-aminopropyltrimethoxysilane,
N-(1,2-bis-t-butyldimethylsiloxycarbonyl)ethyl-N-phenyl-3-aminopropylmethyldimethoxysilane,
N-(1,2-bis-t-butyldimethylsiloxycarbonyl)ethyl-N-phenyl-3-aminopropyldimethylmethoxysilane,
N-(1,2-bis-t-butyldimethylsiloxycarbonyl)ethyl-N-phenyl-3-aminopropyltriethoxysilane,
N-(1,2-bis-t-butyldimethylsiloxycarbonyl)ethyl-N-phenyl-3-aminopropylmethyldiethoxysilane,
N-(1,2-bis-t-butyldimethylsiloxycarbonyl)ethyl-N-phenyl-3-aminopropyldimethylethoxysilane,
N-(2-t-butyldimethylsiloxycarbonyl)ethyl-N-trimethylsilyl-3-aminopropyltrimethoxysilane,
N-(2-t-butyldimethylsiloxycarbonyl)ethyl-N-trimethylsilyl-3-aminopropylmethyldimethoxysilane,
N-(2-t-butyldimethylsiloxycarbonyl)ethyl-N-trimethylsilyl-3-aminopropyldimethylmethoxysilane,
N-(2-t-butyldimethylsiloxycarbonyl)ethyl-N-trimethylsilyl-3-aminopropyltriethoxysilane,
N-(2-t-butyldimethylsiloxycarbonyl)ethyl-N-trimethylsilyl-3-aminopropylmethyldiethoxysilane,
N-(2-t-butyldimethylsiloxycarbonyl)ethyl-N-trimethylsilyl-3-aminopropyldimethylethoxysilane,
N-(2-t-butyldimethylsiloxycarbonyl-2-methyl)ethyl-N-trimethylsilyl-3-aminopropyltrimethoxysilane,
N-(2-t-butyldimethylsiloxycarbonyl-2-methyl)ethyl-N-trimethylsilyl-3-aminopropylmethyldimethoxysilane,
N-(2-t-butyldimethylsiloxycarbonyl-2-methyl)ethyl-N-trimethylsilyl-3-aminopropyldimethylmethoxysilane,
N-(2-t-butyldimethylsiloxycarbonyl-2-methyl)ethyl-N-trimethylsilyl-3-aminopropyltriethoxysilane,
N-(2-t-butyldimethylsiloxycarbonyl-2-methyl)ethyl-N-trimethylsilyl-3-aminopropylmethyldiethoxysilane,
N-(2-t-butyldimethylsiloxycarbonyl-2-methyl)ethyl-N-trimethylsilyl-3-aminopropyldimethylethoxysilane,
N-(1,2-bis-t-butyldimethylsiloxycarbonyl)ethyl-N-trimethylsilyl-3-aminopropyltrimethoxysilane,
N-(1,2-bis-t-butyldimethylsiloxycarbonyl)ethyl-N-trimethylsilyl-3-aminopropylmethyldimethoxysilane,
N-(1,2-bis-t-butyldimethylsiloxycarbonyl)ethyl-N-trimethylsilyl-3-aminopropyldimethylmethoxysilane,
N-(1,2-bis-t-butyldimethylsiloxycarbonyl)ethyl-N-trimethylsilyl-3-aminopropyltriethoxysilane,
N-(1,2-bis-t-butyldimethylsiloxycarbonyl)ethyl-N-trimethylsilyl-3-aminopropylmethyldiethoxysilane,
N-(1,2-bis-t-butyldimethylsiloxycarbonyl)ethyl-N-trimethylsilyl-3-aminopropyldimethylethoxysilane,
N-(2-triisopropylsiloxycarbonyl)ethyl-3-aminopropyltrimethoxysilane, N-(2-triisopropylsiloxycarbonyl)ethyl-3-aminopropylmethyl-dimethoxysilane,
N-(2-triisopropylsiloxycarbonyl)ethyl-3-aminopropyldimethyl-methoxysilane,
N-(2-triisopropylsiloxycarbonyl)ethyl-3-aminopropyltriethoxy-silane,
N-(2-triisopropylsiloxycarbonyl)ethyl-3-aminopropylmethyl-diethoxysilane,
N-(2-triisopropylsiloxycarbonyl)ethyl-3-aminopropyldimethyl-ethoxysilane,
N-(2-triisopropylsiloxycarbonyl-2-methyl)ethyl-3-aminopropyl-trimethoxysilane,
N-(2-triisopropylsiloxycarbonyl-2-methyl)ethyl-3-aminopropyl-methyldimethoxysilane,
N-(2-triisopropylsiloxycarbonyl-2-methyl)ethyl-3-aminopropyl-dimethylmethoxysilane,
N-(2-triisopropylsiloxycarbonyl-2-methyl)ethyl-3-aminopropyl-triethoxysilane,
N-(2-triisopropylsiloxycarbonyl-2-methyl)ethyl-3-aminopropyl-methyldiethoxysilane,
N-(2-triisopropylsiloxycarbonyl-2-methyl)ethyl-3-aminopropyl-dimethylethoxysilane,
N-(1,2-bistriisopropylsiloxycarbonyl)ethyl-3-aminopropyl-trimethoxysilane,
N-(1,2-bistriisopropylsiloxycarbonyl)ethyl-3-aminopropyl-methyldimethoxysilane,
N-(1,2-bistriisopropylsiloxycarbonyl)ethyl-3-aminopropyl-dimethylmethoxysilane,
N-(1,2-bistriisopropylsiloxycarbonyl)ethyl-3-aminopropyl-triethoxysilane,
N-(1,2-bistriisopropylsiloxycarbonyl)ethyl-3-aminopropyl-methyldiethoxysilane,
N-(1,2-bistriisopropylsiloxycarbonyl)ethyl-3-aminopropyl-dimethylethoxysilane,
N-(2-triisopropylsiloxycarbonyl)ethyl-N-methyl-3-aminopropyl-trimethoxysilane,
N-(2-triisopropylsiloxycarbonyl)ethyl-N-methyl-3-aminopropyl-methyldimethoxysilane,
N-(2-triisopropylsiloxycarbonyl)ethyl-N-methyl-3-aminopropyl-dimethylmethoxysilane,
N-(2-triisopropylsiloxycarbonyl)ethyl-N-methyl-3-aminopropyl-triethoxysilane,
N-(2-triisopropylsiloxycarbonyl)ethyl-N-methyl-3-aminopropyl-methyldiethoxysilane,
N-(2-triisopropylsiloxycarbonyl)ethyl-N-methyl-3-aminopropyl-dimethylethoxysilane,
N-(2-triisopropylsiloxycarbonyl-2-methyl)ethyl-N-methyl-3-aminopropyltrimethoxysilane,
N-(2-triisopropylsiloxycarbonyl-2-methyl)ethyl-N-methyl-3-aminopropylmethyldimethoxysilane,
N-(2-triisopropylsiloxycarbonyl-2-methyl)ethyl-N-methyl-3-aminopropyldimethylmethoxysilane,
N-(2-triisopropylsiloxycarbonyl-2-methyl)ethyl-N-methyl-3-aminopropyltriethoxysilane,
N-(2-triisopropylsiloxycarbonyl-2-methyl)ethyl-N-methyl-3-aminopropylmethyldiethoxysilane,
N-(2-triisopropylsiloxycarbonyl-2-methyl)ethyl-N-methyl-3-aminopropyldimethylethoxysilane,
N-(1,2-bistriisopropylsiloxycarbonyl)ethyl-N-methyl-3-aminopropyltrimethoxysilane,
N-(1,2-bistriisopropylsiloxycarbonyl)ethyl-N-methyl-3-aminopropylmethyldimethoxysilane,
N-(1,2-bistriisopropylsiloxycarbonyl)ethyl-N-methyl-3-aminopropyldimethylmethoxysilane,
N-(1,2-bistriisopropylsiloxycarbonyl)ethyl-N-methyl-3-aminopropyltriethoxysilane,
N-(1,2-bistriisopropylsiloxycarbonyl)ethyl-N-methyl-3-aminopropylmethyldiethoxysilane,
N-(1,2-bistriisopropylsiloxycarbonyl)ethyl-N-methyl-3-aminopropyldimethylethoxysilane,
N-(2-triisopropylsiloxycarbonyl)ethyl-N-ethyl-3-aminopropyl-trimethoxysilane,
N-(2-triisopropylsiloxycarbonyl)ethyl-N-ethyl-3-aminopropyl-methyldimethoxysilane,
N-(2-triisopropylsiloxycarbonyl)ethyl-N-ethyl-3-aminopropyl-dimethylmethoxysilane,
N-(2-triisopropylsiloxycarbonyl)ethyl-N-ethyl-3-aminopropyl-triethoxysilane,
N-(2-triisopropylsiloxycarbonyl)ethyl-N-ethyl-3-aminopropyl-methyldiethoxysilane,
N-(2-triisopropylsiloxycarbonyl)ethyl-N-ethyl-3-aminopropyl-dimethylethoxysilane,
N-(2-triisopropylsiloxycarbonyl-2-methyl)ethyl-N-ethyl-3-aminopropyltrimethoxysilane,
N-(2-triisopropylsiloxycarbonyl-2-methyl)ethyl-N-ethyl-3-aminopropylmethyldimethoxysilane,
N-(2-triisopropylsiloxycarbonyl-2-methyl)ethyl-N-ethyl-3-aminopropyldimethylmethoxysilane,
N-(2-triisopropylsiloxycarbonyl-2-methyl)ethyl-N-ethyl-3-aminopropyltriethoxysilane,
N-(2-triisopropylsiloxycarbonyl-2-methyl)ethyl-N-ethyl-3-aminopropylmethyldiethoxysilane,
N-(2-triisopropylsiloxycarbonyl-2-methyl)ethyl-N-ethyl-3-aminopropyldimethylethoxysilane,
N-(1,2-bistriisopropylsiloxycarbonyl)ethyl-N-ethyl-3-aminopropyltrimethoxysilane,
N-(1,2-bistriisopropylsiloxycarbonyl)ethyl-N-ethyl-3-aminopropylmethyldimethoxysilane,
N-(1,2-bistriisopropylsiloxycarbonyl)ethyl-N-ethyl-3-aminopropyldimethylmethoxysilane,
N-(1,2-bistriisopropylsiloxycarbonyl)ethyl-N-ethyl-3-aminopropyltriethoxysilane,
N-(1,2-bistriisopropylsiloxycarbonyl)ethyl-N-ethyl-3-aminopropylmethyldiethoxysilane,
N-(1,2-bistriisopropylsiloxycarbonyl)ethyl-N-ethyl-3-aminopropyldimethylethoxysilane,
N-(2-triisopropylsiloxycarbonyl)ethyl-N-phenyl-3-aminopropyl-trimethoxysilane,
N-(2-triisopropylsiloxycarbonyl)ethyl-N-phenyl-3-aminopropyl-methyldimethoxysilane,
N-(2-triisopropylsiloxycarbonyl)ethyl-N-phenyl-3-aminopropyl-dimethylmethoxysilane,
N-(2-triisopropylsiloxycarbonyl)ethyl-N-phenyl-3-aminopropyl-triethoxysilane,
N-(2-triisopropylsiloxycarbonyl)ethyl-N-phenyl-3-aminopropyl-methyldiethoxysilane,
N-(2-triisopropylsiloxycarbonyl)ethyl-N-phenyl-3-aminopropyl-dimethylethoxysilane,
N-(2-triisopropylsiloxycarbonyl-2-methyl)ethyl-N-phenyl-3-aminopropyltrimethoxysilane,
N-(2-triisopropylsiloxycarbonyl-2-methyl)ethyl-N-phenyl-3-aminopropylmethyldimethoxysilane,
N-(2-triisopropylsiloxycarbonyl-2-methyl)ethyl-N-phenyl-3-aminopropyldimethylmethoxysilane,
N-(2-triisopropylsiloxycarbonyl-2-methyl)ethyl-N-phenyl-3-aminopropyltriethoxysilane,
N-(2-triisopropylsiloxycarbonyl-2-methyl)ethyl-N-phenyl-3-aminopropylmethyldiethoxysilane,
N-(2-triisopropylsiloxycarbonyl-2-methyl)ethyl-N-phenyl-3-aminopropyldimethylethoxysilane,
N-(1,2-bistriisopropylsiloxycarbonyl)ethyl-N-phenyl-3-aminopropyltrimethoxysilane, N-(1,2-bistriisopropylsiloxycarbonyl)ethyl-N-phenyl-3-aminopropylmethyldimethoxysilane,
N-(1,2-bistriisopropylsiloxycarbonyl)ethyl-N-phenyl-3-aminopropyldimethylmethoxysilane,
N-(1,2-bistriisopropylsiloxycarbonyl)ethyl-N-phenyl-3-aminopropyltriethoxysilane,
N-(1,2-bistriisopropylsiloxycarbonyl)ethyl-N-phenyl-3-aminopropylmethyldiethoxysilane,
N-(1,2-bistriisopropylsiloxycarbonyl)ethyl-N-phenyl-3-aminopropyldimethylethoxysilane,
N-(2-triisopropylsiloxycarbonyl)ethyl-N-trimethylsilyl-3-aminopropyltrimethoxysilane,
N-(2-triisopropylsiloxycarbonyl)ethyl-N-trimethylsilyl-3-aminopropylmethyldimethoxysilane,
N-(2-triisopropylsiloxycarbonyl)ethyl-N-trimethylsilyl-3-aminopropyldimethylmethoxysilane,
N-(2-triisopropylsiloxycarbonyl)ethyl-N-trimethylsilyl-3-aminopropyltriethoxysilane,
N-(2-triisopropylsiloxycarbonyl)ethyl-N-trimethylsilyl-3-aminopropylmethyldiethoxysilane,
N-(2-triisopropylsiloxycarbonyl)ethyl-N-trimethylsilyl-3-aminopropyldimethylethoxysilane,
N-(2-triisopropylsiloxycarbonyl-2-methyl)ethyl-N-trimethylsilyl-3-aminopropyltrimethoxysilane,
N-(2-triisopropylsiloxycarbonyl-2-methyl)ethyl-N-trimethylsilyl-3-aminopropylmethyldimethoxysilane,
N-(2-triisopropylsiloxycarbonyl-2-methyl)ethyl-N-trimethylsilyl-3-aminopropyldimethylmethoxysilane,
N-(2-triisopropylsiloxycarbonyl-2-methyl)ethyl-N-trimethylsilyl-3-aminopropyltriethoxysilane,
N-(2-triisopropylsiloxycarbonyl-2-methyl)ethyl-N-trimethylsilyl-3-aminopropylmethyldiethoxysilane,
N-(2-triisopropylsiloxycarbonyl-2-methyl)ethyl-N-trimethylsilyl-3-aminopropyldimethylethoxysilane,
N-(1,2-bistriisopropylsiloxycarbonyl)ethyl-N-trimethylsilyl-3-aminopropyltrimethoxysilane,
N-(1,2-bistriisopropylsiloxycarbonyl)ethyl-N-trimethylsilyl-3-aminopropylmethyldimethoxysilane,
N-(1,2-bistriisopropylsiloxycarbonyl)ethyl-N-trimethylsilyl-3-aminopropyldimethylmethoxysilane,
N-(1,2-bistriisopropylsiloxycarbonyl)ethyl-N-trimethylsilyl-3-aminopropyltriethoxysilane,
N-(1,2-bistriisopropylsiloxycarbonyl)ethyl-N-trimethylsilyl-3-aminopropylmethyldiethoxysilane,
N-(1,2-bistriisopropylsiloxycarbonyl)ethyl-N-trimethylsilyl-3-aminopropyldimethylethoxysilane, etc.

The de-triorganosilylation reaction may be carried out, for example, using a compound having active hydrogen. Suitable compounds having active hydrogen include alcohols such as methanol, ethanol, and isopropyl alcohol, phenols such as phenol, cresol and xylenol, carboxylic acids such as formic acid, acetic acid, and propionic acid, and mineral acids such as hydrochloric acid, sulfuric acid, and nitric acid.

The compound of formula (2) and the compound having active hydrogen may be combined in any desired ratio. From the standpoints of reactivity and productivity, the compound having active hydrogen is preferably used in such an amount as to give 0.5 to 100 moles, more preferably 1 to 20 moles of active hydrogen per mole of triorganosilyl group on the compound of formula (2).

Although the reaction conditions are not particularly limited, the reaction temperature is preferably 0 to 200° C., more preferably 10 to 150° C., and the reaction time is preferably 1 to 40 hours, more preferably 1 to 20 hours.

A solvent may be used for the reaction although the reaction may run in the absence of solvent. Suitable solvents include hydrocarbon solvents such as pentane, hexane, cyclohexane, heptane, isooctane, benzene, toluene, and xylene, ether solvents such as diethyl ether, tetrahydrofuran and dioxane, ester solvents such as ethyl acetate and butyl acetate, aprotic polar solvents such as acetonitrile, N,N-dimethylformamide, and N-methylpyrrolidone, and chlorinated hydrocarbon solvents such as dichloromethane and chloroform. The solvents may be used alone or in admixture of two or more.

From the resulting reaction solution, the target compound may be recovered by standard techniques such as filtration, solvent washing and recrystallization. On use, the compound may be dissolved in a suitable solvent.

EXAMPLE

Examples of the invention are given below by way of illustration and not by way of limitation.

Synthesis Example 1

Synthesis of N-(2-triisopropylsiloxycarbonyl)ethyl-3-aminopropyltrimethoxysilane A flask equipped with a stirrer, reflux condenser, dropping funnel and thermometer was charged with 179.3 g (1.0 mol) of 3-aminopropyltrimethoxysilane and 17.9 g of acetonitrile and heated at 70° C. Once the internal temperature became steady, 228.4 g (1.0 mol) of triisopropylsilyl acrylate was added dropwise over 2 hours, followed by stirring at the temperature for 3 hours. Then the low-boiling fraction was removed under a pressure of 0.4 kPa, obtaining 425.3 g of N-(2-triisopropylsiloxycarbonyl)ethyl-3-aminopropyltrimethoxysilane as a colorless clear liquid.

Example 1

Synthesis of N-(3-trimethoxysilylpropyl)-β-alanine from N-(2-triisopropylsiloxycarbonyl)ethyl-3-aminopropyl-trimethoxysilane A flask equipped with a stirrer, reflux condenser, dropping funnel and thermometer was charged with 122.3 g (0.3 mol) of N-(2-triisopropylsiloxycarbonyl)ethyl-3-aminopropyl-trimethoxysilane in Synthesis Example 1 and heated at 50° C. Once the internal temperature became steady, 10.6 g (0.33 mol) of methanol was added dropwise over 1 hour. The reaction solution was stirred at the temperature for 6 hours. The resulting solid was collected by filtration, washed with 200 ml of hexane, and dried in vacuum. There was obtained 50.4 g of a white solid.

Figure 2:
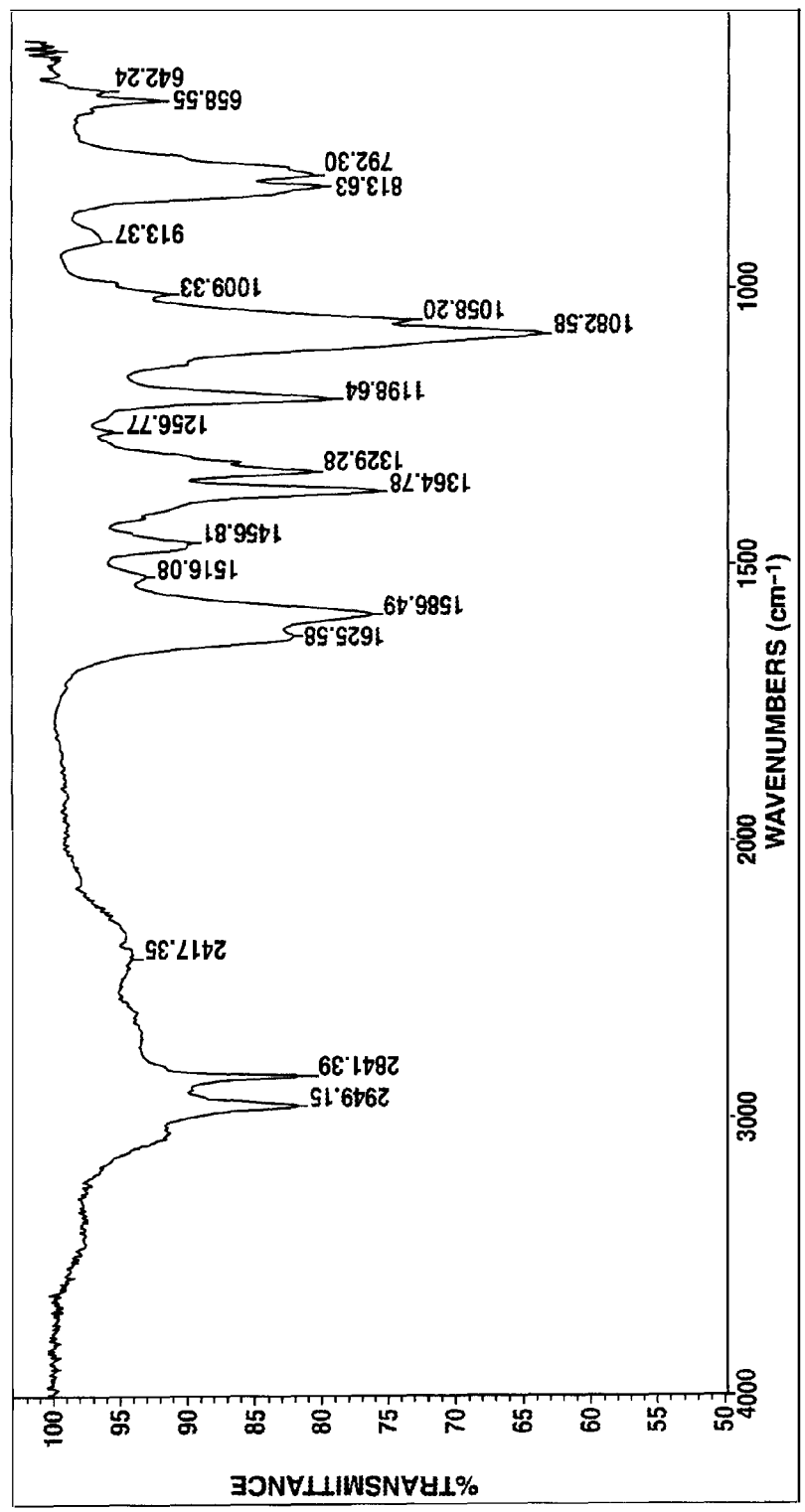

The solid was analyzed by $^1$H-NMR and IR spectroscopy. FIGS. 1 and 2 show $^1$H-NMR spectrum (heavy methanol solvent) and IR spectrum, respectively. With these data, the compound was identified to be N-(3-trimethoxysilylpropyl)-β-alanine.

Synthesis Example 2

Synthesis of N-(2-triisopropylsiloxycarbonyl)ethyl-3-aminopropylmethyldimethoxysilane A flask equipped with a stirrer, reflux condenser, dropping funnel and thermometer was charged with 163.3 g (1.0 mol) of 3-aminopropylmethyldimethoxysilane and heated at 70° C. Once the internal temperature became steady, 228.4 g (1.0 mol) of triisopropylsilyl acrylate was added dropwise over 1 hour, followed by stirring at the temperature for 6 hours.

There was obtained 391.2 g of N-(2-triisopropylsiloxycarbonyl)ethyl-3-aminopropylmethyldimethoxysilane as a pale yellow clear liquid.

Example 2

Synthesis of N-(3-methyldimethoxysilylpropyl)-β-alanine from N-(2-triisopropylsiloxycarbonyl)ethyl-3-aminopropyl-methyldimethoxysilane A flask equipped with a stirrer, reflux condenser, dropping funnel and thermometer was charged with 117.5 g (0.3 mol) of N-(2-triisopropylsiloxycarbonyl)ethyl-3-aminopropyl-methyldimethoxysilane in Synthesis Example 2 and heated at 50° C. Once the internal temperature became steady, 10.6 g (0.33 mol) of methanol was added dropwise over 1 hour. The reaction solution was stirred at the temperature for 6 hours. The resulting solid was collected by filtration, washed with 200 ml of hexane, and dried in vacuum. There was obtained 68.8 g of a white solid.

Figure 3:
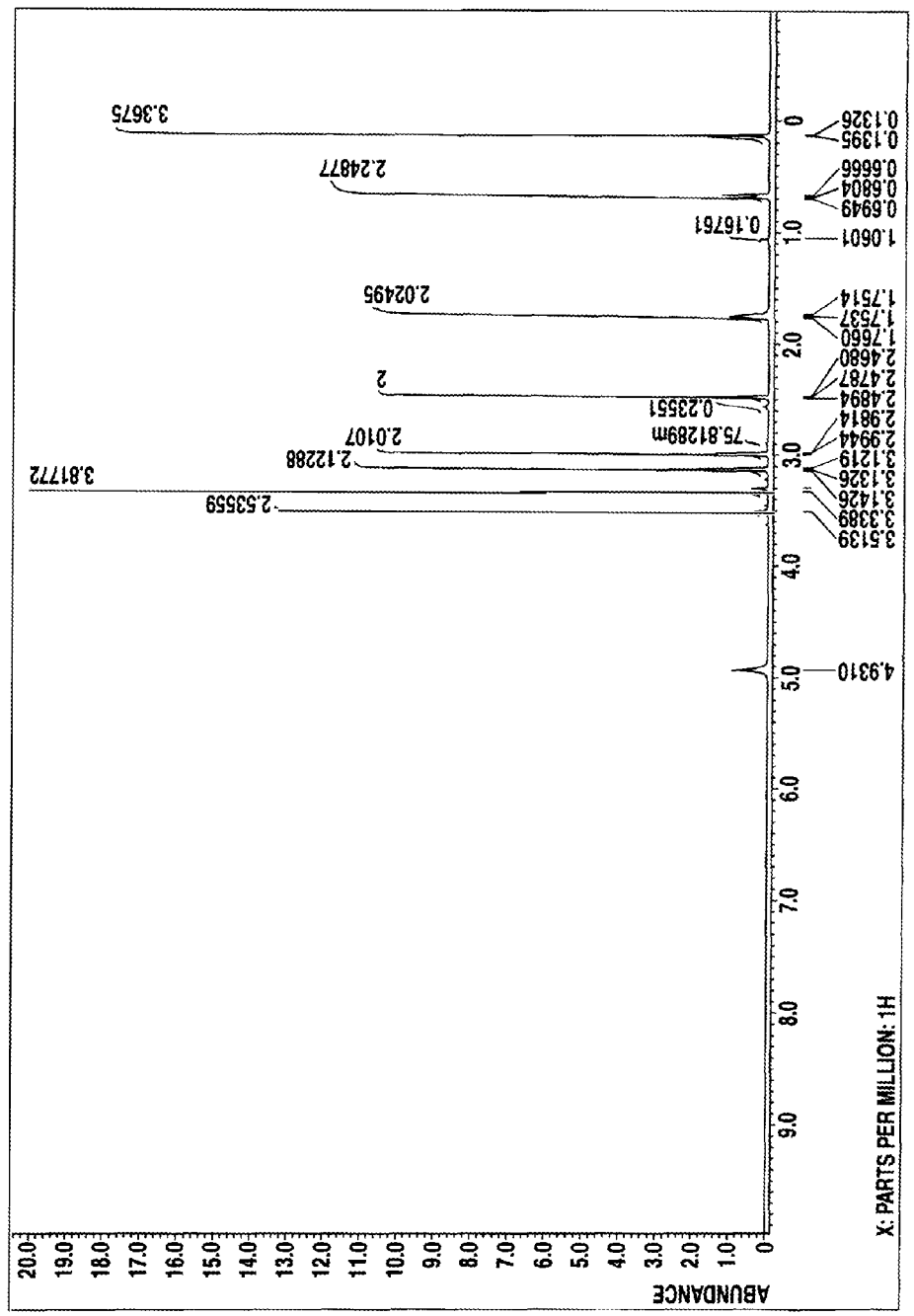
FIGS. 3 and 4 are $^1$H-NMR and IR spectra of N-(3-methyldimethoxysilylpropyl)-β-alanine obtained in Example 2, respectively.
Figure 4:
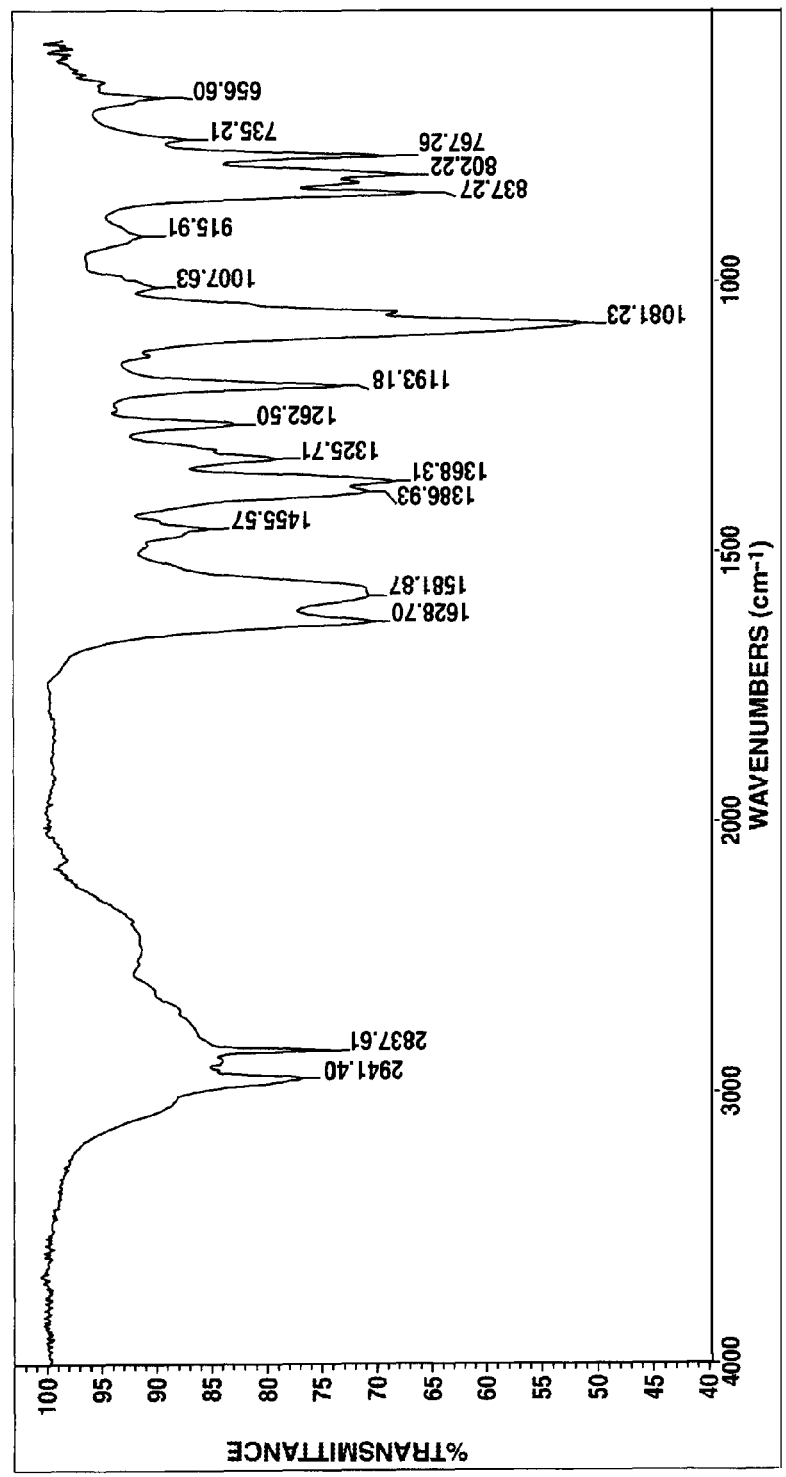

The solid was analyzed by $^1$H-NMR and IR spectroscopy. FIGS. 3 and 4 show $^1$H-NMR spectrum (heavy methanol solvent) and IR spectrum, respectively. With these data, the compound was identified to be N-(3-methyldimethoxysilylpropyl)-β-alanine.

Synthesis Example 3

Synthesis of N-(2-triisopropylsiloxycarbonyl)ethyl-3-aminopropyltriethoxysilane

A flask equipped with a stirrer, reflux condenser, dropping funnel and thermometer was charged with 221.4 g (1.0 mol) of 3-aminopropyltriethoxysilane and heated at 70° C. Once the internal temperature became steady, 228.4 g (1.0 mol) of triisopropylsilyl acrylate was added dropwise over 1 hour, followed by stirring at the temperature for 6 hours. There was obtained 449.1 g of N-(2-triisopropylsiloxycarbonyl)ethyl-3-aminopropyltriethoxysilane as a pale yellow clear liquid.

Example 3

Synthesis of N-(3-triethoxysilylpropyl)-β-alanine from N-(2-triisopropylsiloxycarbonyl)ethyl-3-aminopropyl-triethoxysilane A flask equipped with a stirrer, reflux condenser, dropping funnel and thermometer was charged with 90.0 g (0.2 mol) of N-(2-triisopropylsiloxycarbonyl)ethyl-3-aminopropyl-triethoxysilane in Synthesis Example 3 and heated at 50° C. Once the internal temperature became steady, 92.2 g (2.0 mol) of ethanol was added dropwise over 1 hour. The reaction solution was stirred at the temperature for 12 hours. At the end of reaction, the excess of ethanol was removed under vacuum. The precipitated solid was collected by filtration, washed with 150 ml of hexane, and dried in vacuum. There was obtained 31.6 g of a white solid.

Figure 5:
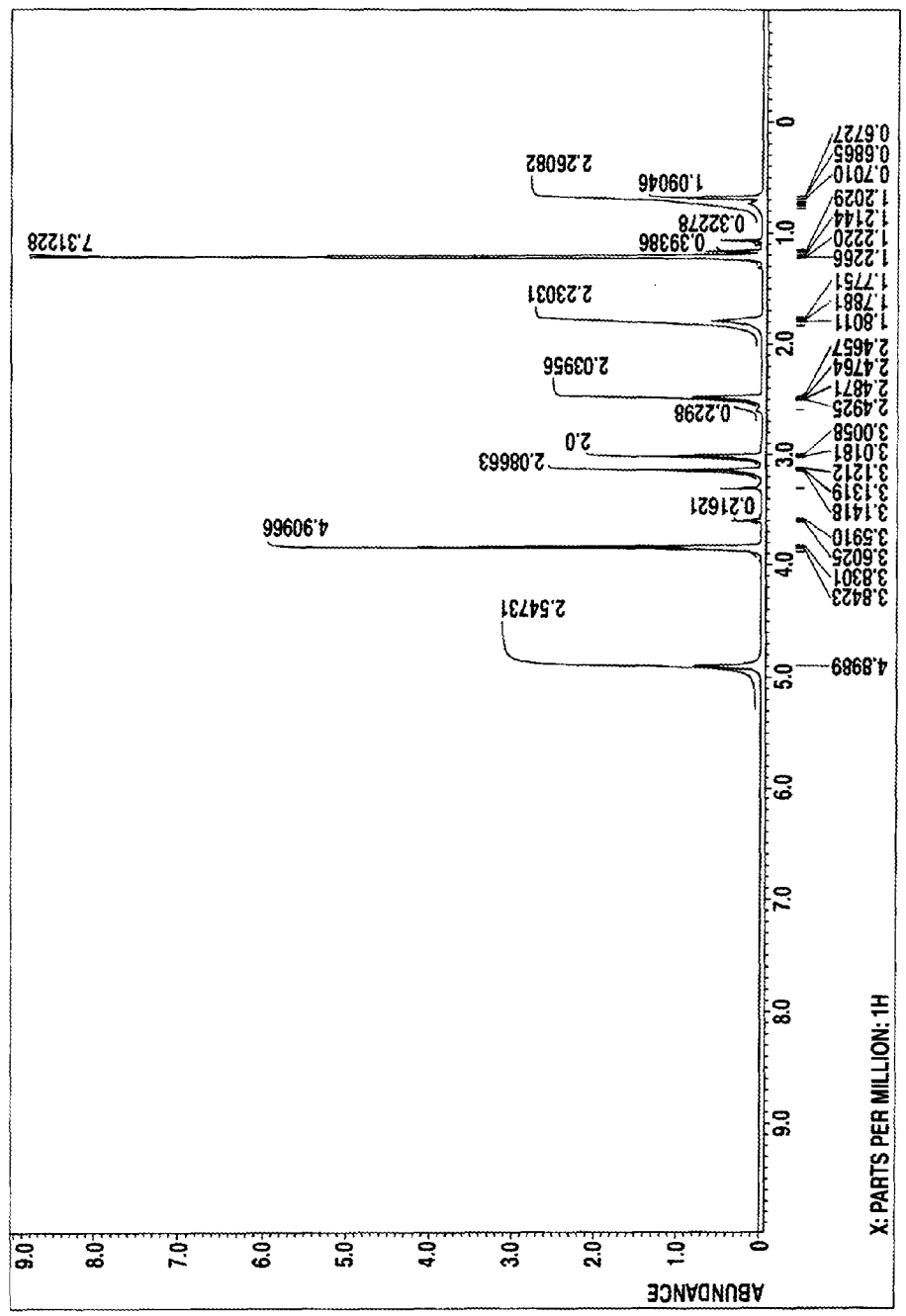
FIGS. 5 and 6 are $^1$H-NMR and IR spectra of N-(3-triethoxysilylpropyl)-β-alanine obtained in Example 3, respectively.
Figure 6:
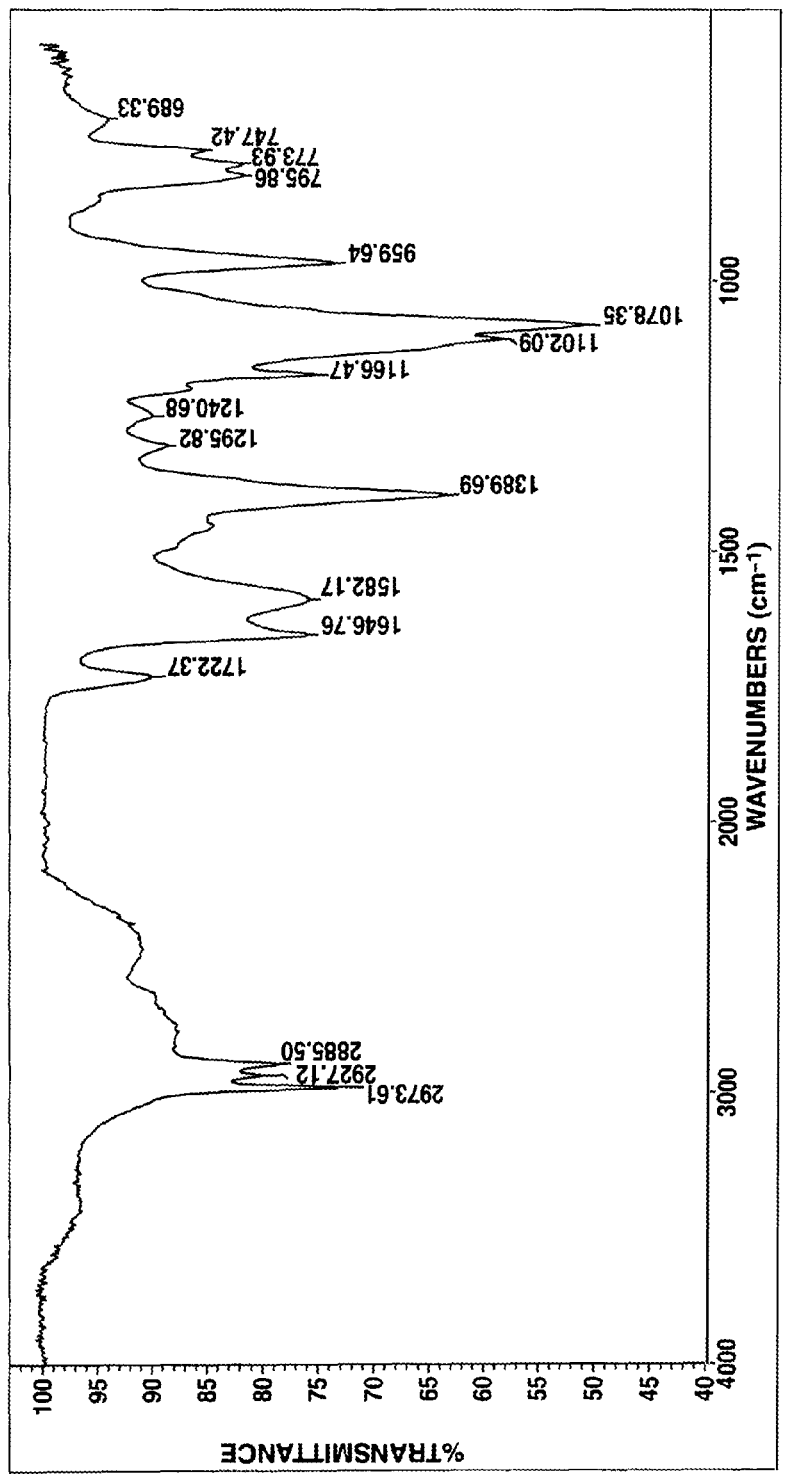

The solid was analyzed by $^1$H-NMR and IR spectroscopy. FIGS. 5 and 6 show $^1$H-NMR spectrum (heavy methanol solvent) and IR spectrum, respectively. With these data, the compound was identified to be N-(3-triethoxysilylpropyl)-β-alanine.

Synthesis Example 4

Synthesis of N-(2-triisopropylsiloxycarbonyl)ethyl-3-aminopropylmethyldiethoxysilane A flask equipped with a stirrer, reflux condenser, dropping funnel and thermometer was charged with 191.3 g (1.0 mol) of 3-aminopropylmethyldiethoxysilane and heated at 70° C. Once the internal temperature became steady, 228.4 g (1.0 mol) of triisopropylsilyl acrylate was added dropwise over 1 hour, followed by stirring at the temperature for 6 hours. There was obtained 419.0 g of N-(2-triisopropylsiloxycarbonyl)ethyl-3-aminopropylmethyldiethoxysilane as a pale yellow clear liquid.

Example 4

Synthesis of N-(3-methyldiethoxysilylpropyl)-β-alanine from N-(2-triisopropylsiloxycarbonyl)ethyl-3-aminopropyl-methyldiethoxysilane A flask equipped with a stirrer, reflux condenser, dropping funnel and thermometer was charged with 84.0 g (0.2 mol) of N-(2-triisopropylsiloxycarbonyl)ethyl-3-aminopropyl-methyldiethoxysilane in Synthesis Example 4 and heated at 50° C. Once the internal temperature became steady, 92.2 g (2.0 mol) of ethanol was added dropwise over 1 hour. The reaction solution was stirred at the temperature for 12 hours. At the end of reaction, the excess of ethanol was removed under vacuum. The precipitated solid was collected by filtration, washed with 150 ml of hexane, and dried in vacuum. There was obtained 35.1 g of a white solid.

Figure 7:
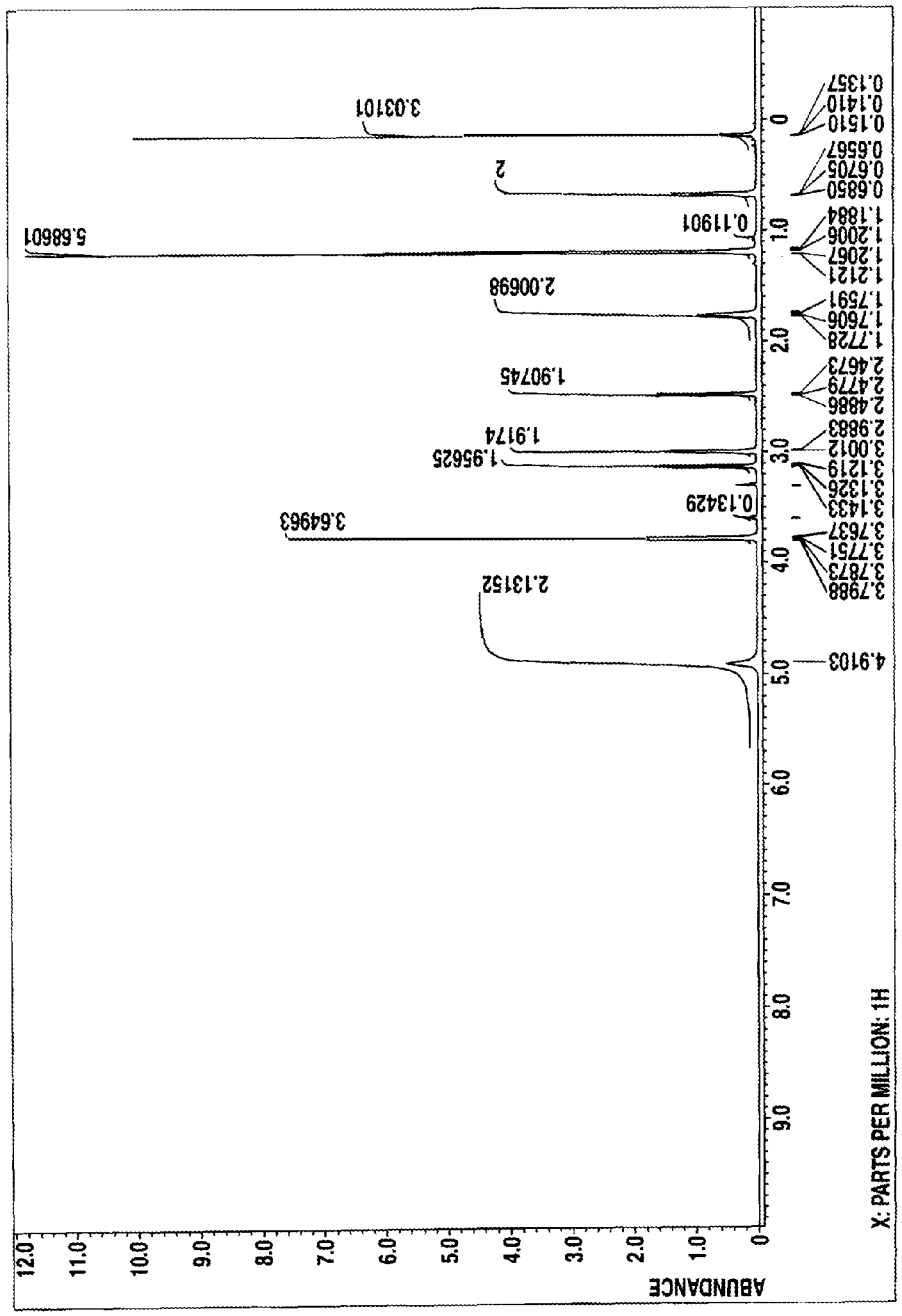
FIGS. 7 and 8 are $^1$H-NMR and IR spectra of N-(3-methyldiethoxysilylpropyl)-β-alanine obtained in Example 4, respectively.
Figure 8:
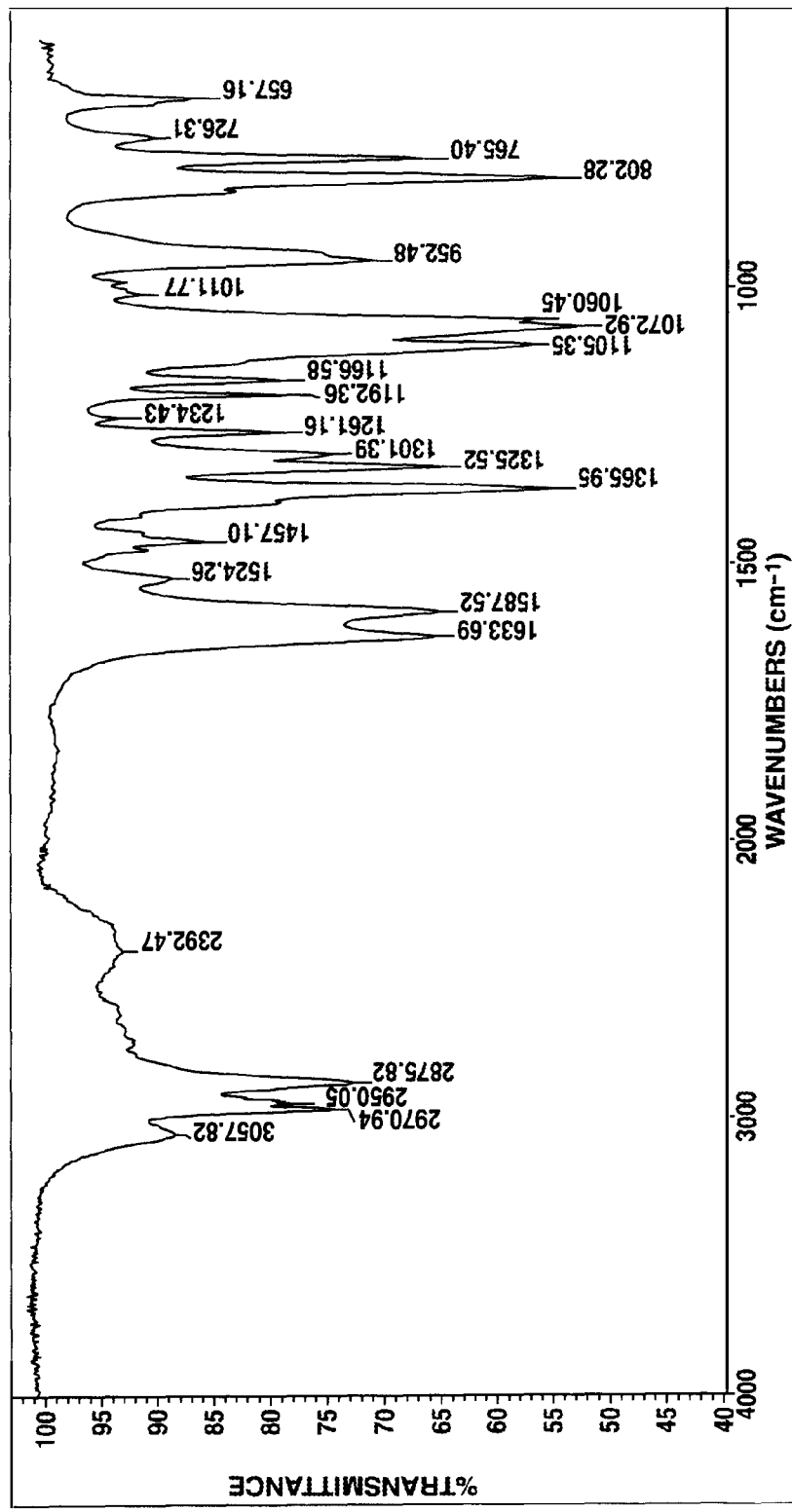

The solid was analyzed by $^1$H-NMR and IR spectroscopy. FIGS. 7 and 8 show $^1$H-NMR spectrum (heavy methanol solvent) and IR spectrum, respectively. With these data, the compound was identified to be N-(3-methyldiethoxysilylpropyl)-β-alanine.

Synthesis Example 5

Synthesis of N-(1,2-bistriisopropylsiloxycarbonyl)ethyl-3-aminopropyltrimethoxysilane A flask equipped with a stirrer, reflux condenser, dropping funnel and thermometer was charged with 17.9 g (0.1 mol) of 3-aminopropyltrimethoxysilane and heated at 70° C. Once the internal temperature became steady, 42.9 g (0.1 mol) of bistriisopropylsilyl maleate was added dropwise over 1 hour, followed by stirring at the temperature for 6 hours. There was obtained 60.4 g of N-(1,2-bistriisopropylsiloxycarbonyl)ethyl-3-aminopropyltrimethoxysilane as a pale yellow clear liquid.

Example 5

Synthesis of N-(3-trimethoxysilylpropyl)aspartic acid from N-(1,2-bistriisopropylsiloxycarbonyl)ethyl-3-aminopropyl-trimethoxysilane A flask equipped with a stirrer, reflux condenser, dropping funnel and thermometer was charged with 30.4 g (0.05 mol) of N-(1,2-bistriisopropylsiloxycarbonyl)ethyl-3-aminopropyltrimethoxysilane in Synthesis Example 5 and heated at 50° C. Once the internal temperature became steady, 3.5 g (0.11 mol) of methanol was added dropwise over 1 hour. The reaction solution was stirred at the temperature for 6 hours.

The resulting solid was collected by filtration, washed with 60 ml of hexane, and dried in vacuum. There was obtained 13.4 g of a white solid.

Figure 9:
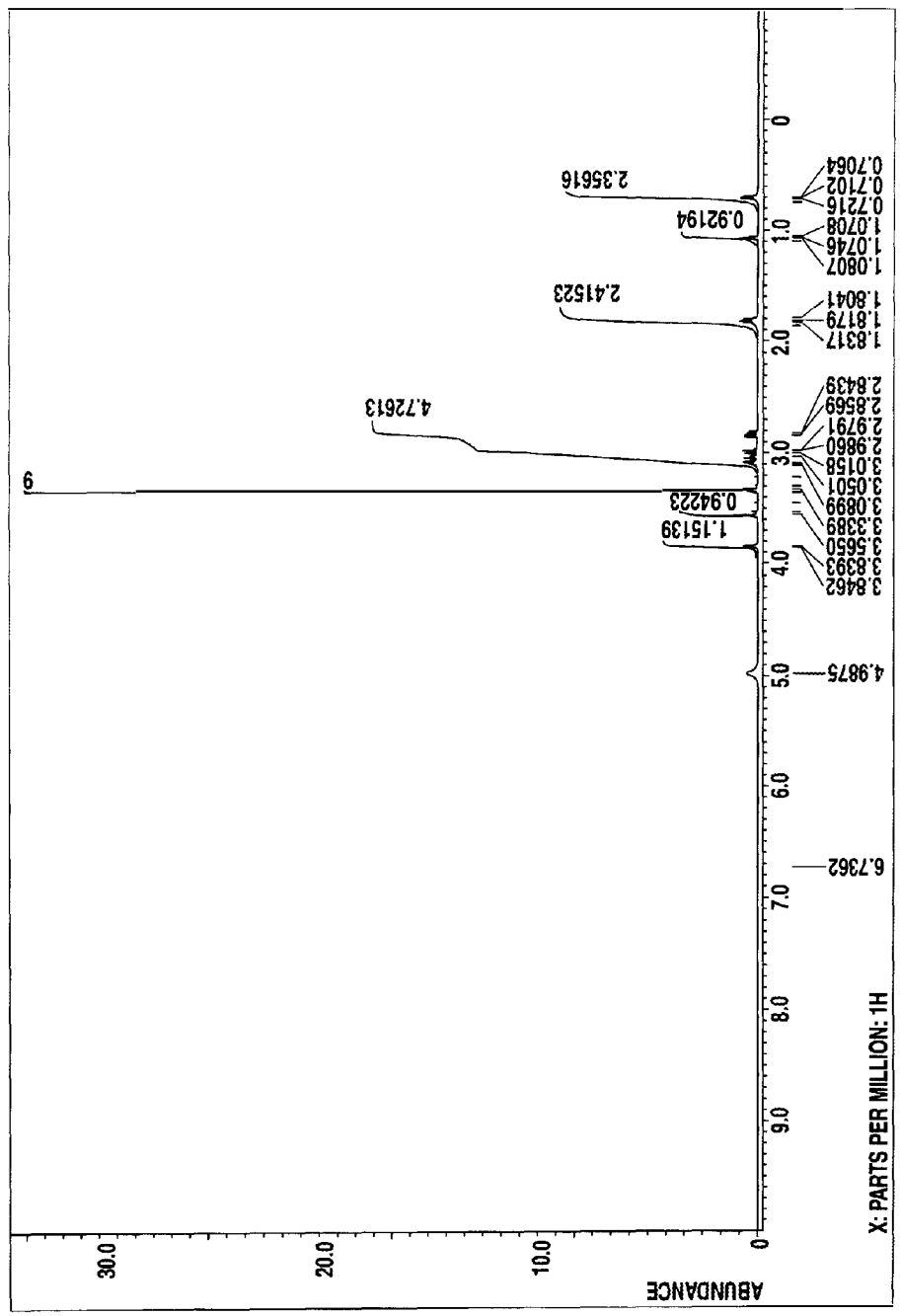
FIGS. 9 and 10 are $^1$H-NMR and IR spectra of N-(3-trimethoxysilylpropyl)aspartic acid obtained in Example 5, respectively.
Figure 10:
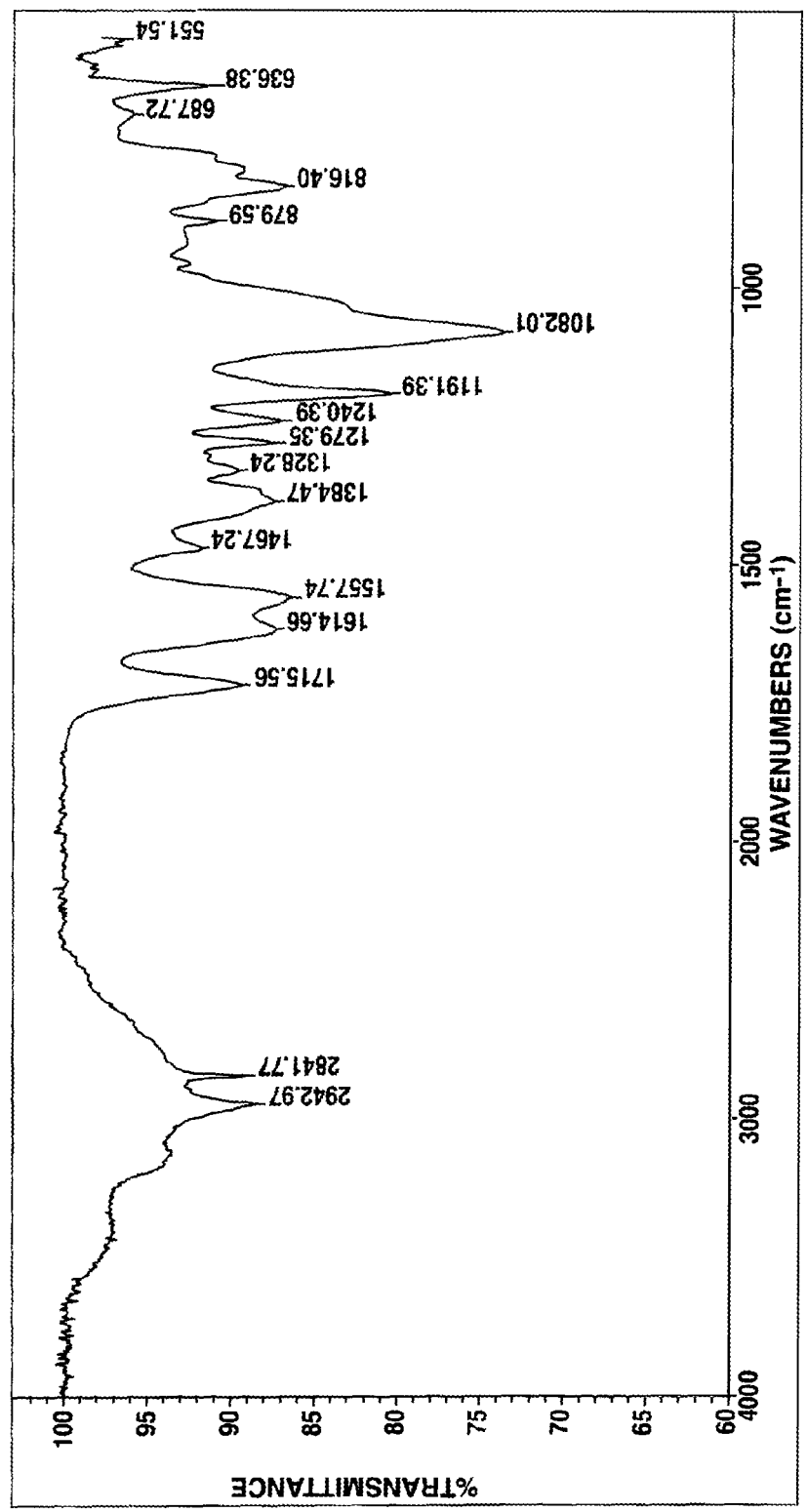

The solid was analyzed by $^1$H-NMR and IR spectroscopy. FIGS. 9 and 10 show $^1$H-NMR spectrum (heavy methanol solvent) and IR spectrum, respectively. With these data, the compound was identified to be N-(3-trimethoxysilylpropyl) aspartic acid.

Synthesis Example 6

Synthesis of N-(2-trimethylsiloxycarbonyl)ethyl-N-trimethylsilyl-3-aminopropyltrimethoxysilane A flask equipped with a stirrer, reflux condenser, dropping funnel and thermometer was charged with 136.8 g (0.5 mol) of N-(2-trimethylsiloxycarbonyl)ethyl-N-trimethylsilyl-allylamine and 0.65 g of a toluene solution of platinum/1,3-divinyl-1,1,3,3-tetramethyldisiloxane complex (platinum content 3 wt %) and heated at 70° C. Once the internal temperature became steady, 61.1 g (0.5 mol) of trimethoxysilane was added dropwise over 1 hour, followed by stirring at the temperature for 5 hours. On distillation of the reaction solution, 128.5 g of N-(2-trimethylsiloxy-carbonyl)ethyl-N-trimethylsilyl-3-aminopropyltrimethoxysilane was obtained as a fraction at a boiling point of 139-140° C./0.4 kPa. Yield 65%.

Example 6

Synthesis of N-(3-trimethoxysilylpropyl)-β-alanine from N-(2-trimethylsiloxycarbonyl)ethyl-N-trimethylsilyl-3-aminopropyltrimethoxysilane A flask equipped with a stirrer, reflux condenser, dropping funnel and thermometer was charged with 72.1 g (0.2 mol) of N-(2-trimethylsiloxycarbonyl)ethyl-N-trimethylsilyl-3-aminopropyltrimethoxysilane in Synthesis Example 6 and heated at 50° C. Once the internal temperature became steady, 14.1 g (0.44 mol) of methanol was added dropwise over 1 hour. The reaction solution was stirred at the temperature for 1 hour. The resulting solid was collected by filtration, washed with 150 ml of hexane, and dried in vacuum. There was obtained 45.0 g of a white solid.

The solid was analyzed by $^1$H-NMR and IR spectroscopy, finding that the spectra were coincident with those of Example 1. The compound was thus identified to be N-(3-trimethoxysilylpropyl)-β-alanine.

Japanese Patent Application Nos. 2011-026789 and 2011-194619 are incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. An amino acid-modified silane compound having the general formula (1):

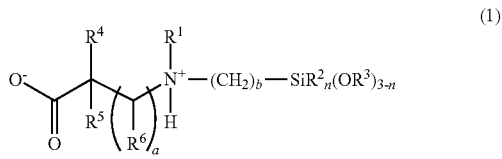

wherein $R^1$, $R^4$ and $R^5$ each are hydrogen, $R^2$ and $R^3$ each are a substituted or unsubstituted, $C_1$-$C_{20}$ monovalent hydrocarbon group, $R^6$ is hydrogen or carboxyl group, a is 1, b is 3, and n is 0, 1 or 2.

2. The silane compound of claim 1, which is
N-(3-trimethoxysilylpropyl)-β-alanine,
N-(3-methyldimethoxysilylpropyl)-β-alanine,
N-(3-triethoxysilylpropyl)-β-alanine,
N-(3-methyldiethoxysilylpropyl)-β-alanine,
N-(3-trimethoxysilylpropyl)aspartic acid,
N-(3-methyldimethoxysilylpropyl)aspartic acid,
N-(3-triethoxysilylpropyl)aspartic acid, or
N-(3-methyldiethoxysilylpropyl)aspartic acid.

3. A method for preparing the amino acid-modified silane compound of claim 1, comprising de-triorganosilylation reaction of a silyl-protected, amino acid-modified silane compound having the general formula (2):

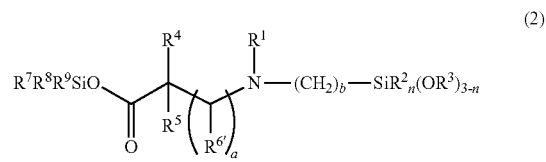

wherein $R^{1'}$ is $R^1$ or a triorganosilyl group of $R^{10}R^{11}R^{12}Si-$, $R^1$, $R^4$ and $R^5$ each are hydrogen, $R^2$ and $R^3$ each are a substituted or unsubstituted, $C_1$-$C_{20}$ monovalent hydrocarbon group, $R^{6'}$ is hydrogen or a silyl-protected carboxyl group, $R^7$, $R^8$, $R^9$, $R^{10}$, $R^{11}$ and $R^{12}$ each are a substituted or unsubstituted, $C_1$-$C_{20}$ monovalent hydrocarbon group, a is 1, b is 3, and n is 0, 1 or 2.

* * * * *